(12) United States Patent
Plesch et al.

(10) Patent No.: US 8,030,539 B2
(45) Date of Patent: Oct. 4, 2011

(54) METHOD FOR THE STABLE EXPRESSION OF NUCLEIC ACIDS IN TRANSGENIC PLANTS, CONTROLLED BY A PARSLEY-UBIQUITIN PROMOTER

(75) Inventors: Gunnar Plesch, Potsdam (DE); Marcus Ebneth, Berlin (DE)

(73) Assignee: Metanomics GmbH & Co. KGaA (DE)

( * ) Notice: Subject to any disclaimer, the term of this patent is extended or adjusted under 35 U.S.C. 154(b) by 956 days.

(21) Appl. No.: 10/515,020

(22) PCT Filed: May 30, 2003

(86) PCT No.: PCT/EP03/05668
§ 371 (c)(1),
(2), (4) Date: Nov. 22, 2004

(87) PCT Pub. No.: WO03/102198
PCT Pub. Date: Dec. 11, 2003

(65) Prior Publication Data
US 2007/0006347 A1    Jan. 4, 2007

(30) Foreign Application Priority Data
Jun. 4, 2002    (DE) .................................. 102 24 889

(51) Int. Cl.
*C12N 15/82* (2006.01)
*C07H 21/04* (2006.01)
*A01H 5/00* (2006.01)
(52) U.S. Cl. ........ 800/278; 800/295; 800/298; 536/24.1
(58) Field of Classification Search ........................ None
See application file for complete search history.

(56) References Cited

U.S. PATENT DOCUMENTS

| | | | |
|---|---|---|---|
| 5,352,605 A | 10/1994 | Fraley et al. | |
| 5,504,200 A | 4/1996 | Hall et al. | |
| 5,510,474 A | 4/1996 | Quail et al. | |
| 5,612,472 A | 3/1997 | Wilson et al. | |
| 5,659,026 A | 8/1997 | Baszczynski et al. | |
| 5,767,379 A * | 6/1998 | Baszczynski et al. | 800/320.1 |
| 6,020,190 A | 2/2000 | Quail et al. | |
| 6,054,574 A | 4/2000 | Quail et al. | |
| 6,177,611 B1 | 1/2001 | Rice | |
| 6,365,728 B1 | 4/2002 | Hodges et al. | |
| 6,504,085 B1 * | 1/2003 | Howard | 800/288 |
| 6,528,701 B1 | 3/2003 | Wang et al. | |

FOREIGN PATENT DOCUMENTS

| | | |
|---|---|---|
| CA | 2348888 | 5/2000 |
| EP | 0 409 625 A1 | 7/1990 |
| WO | WO-91/13991 | 9/1991 |
| WO | WO-92/16635 | 10/1992 |
| WO | WO-94/21794 | 9/1994 |
| WO | WO-97/05900 | 2/1997 |
| WO | WO-98/22593 | 5/1998 |
| WO | WO-00/26388 | 5/2000 |
| WO | WO-00/37662 A3 | 6/2000 |
| WO | WO-01/18220 A1 | 3/2001 |
| WO | WO-03/008596 A2 | 1/2003 |

OTHER PUBLICATIONS

Kawalleck et al. Polyubiquitin gene expression and structural propertides of the Ubi4-2 gene in *Petroselinum crispum*. (1993) PMB, vol. 21, pp. 673-684.*
Weisshaar, B. P. crispum gene Pcubi4-2 for polyubiquitin. (1994) GenBank Accession X64345.1, pp. 1-2.*
Yokoi et al. Introduction of the cDNA for Arabidopsis glycerol-3-phosphate acyltransferase (GPAT) confers unsaturation of fatty acids and chilling tolerance of phtosynthesis on rice. (1998) Molecular Breeding; vol. 4, pp. 269-275.*
Khan et al. Expression of Bt gene in a dicot plant under promoter derived from a monocot plant. (2001) Pakistan J. of Biol. Sci.; vol. 4, pp. 1518-1522.*
Gandhi et al. Transient gene expression and influence of promoters on foreign gene expression in *Arabidopsis thaliana*. (1999) In Vitro Cell. Dev. Biol.; vol. 35; pp. 232-237.*
Christensen et al. Maize polyubiquitin genes: structure, thermal perturbation of expression and transcript splicing, and promoter activity following transfer to protoplasts by electroporation. (1992) PMB, vol. 18; pp. 675-689.*
Kawalleck, P. et al., "Polyubiquitin gene expression and structural properties of the *ubi*4-2 gene in *Petroselinum crispum*." Plant Molecular Biology, vol. 21, pp. 673-684, (1993).
Christensen, A. H. et al., "Maize polyubiquitin genes: structure, thermal perturbation of expression and transcript splicing, and promotor activity following transfer to protoplasts by electroporation." Plant Molecular Biology, vol. 18, pp. 675-689, (1992).
Binet, M. et al., "Analysis of a sunflower polyubiquitin promotor by transient expression." Plant Science, vol. 79, pp. 87-94 (1991). Wang, J. et al., "Structure, expression and promotor activity of two polyubiquitin genes from rice (*Oryza sativa* L.)." Plant Science, vol. 156, pp. 201-211 (2000).
Holtorf, S. et al., "Comparison of different constitutive and inducible promoters for the overexpression of transgenes in *Arabidopsis thaliana*." Plant Molecular Biology, vol. 29, pp. 637-646 (1995).
Hill-Ambroz, K. L. et al., "Constitutive promoter expression of transgenes in wheat (*Triticum aestivum*)." Cereal Research Communications, vol. 29, Nos. 1-2, pp. 9-16 (2001).
Hill-Ambroz, K. L. et al., "Comparison of constitutive promoters for sorghum [*Sorghum bicolor* (L.) Moench] transformation." Cereal Research Communications, vol. 29, Nos. 1-2, pp. 17-24 (2001).
Zhang, W. et al., "Analysis of rice Act1 5' region activity in transgenic rice plants." The Plant Cell, vol. 3, pp. 1155-1165 (1991).
Cushman, J. C. et al., "Expression of a phosphoenolpyruvate carboxylase promoter from *Mesembryanthemum crystallinum* is not salt-inducible in mature transgenic tobacco." Plant Molecular Biology, vol. 21, pp. 561-566 (1993).
Halford, N. G. et al., "Genetically modified crops: methodology, benefits, regulation and public concerns." British Medical Bulletin, vol. 56, No. 1, pp. 62-73 (2000).

(Continued)

*Primary Examiner* — Cathy Kingdon Worley
(74) *Attorney, Agent, or Firm* — Connolly Bove Lodge & Hutz LLP

(57) ABSTRACT

The invention relates to a method for the stable expression of nucleic acids in transgenic plants, controlled by a parsley-ubiquitin promoter (PCUbi4-2). Said promoter, isolated from parsley (petroselinum crispum) exhibits in almost all transgenic plants an intensely constitutive expression in almost all vegetable tissue, including the seed. It also contains, among others, a potentially heat-shock inducible element (HSE). The invention also relates to nucleic acid constructs, vectors and transgenic plants and to the use of the latter for producing foodstuffs, animal feed, seeds, pharmaceuticals or fine chemicals.

24 Claims, 8 Drawing Sheets

OTHER PUBLICATIONS

Dunwell J. M., "Transgenic approaches to crop improvement." Journal of Experimental Botany, vol. 51, GMP Special Issue, pp. 487-496 (2000).

Vaeck, M. et al., "Transgenic plants protected from insect attack." Nature, vol. 328, No. 2, pp. 33-37 (1987).

Broglie, K. et al., "Transgenic plants with enhanced resistance to the fungal pathogen *Rhizoctonia solani*." Science, vol. 254, pp. 1194-1197 (1991).

Ott, K. et al., "Rational molecular design and genetic engineering of herbicide resistant crops by structure modeling and site-directed mutagenesis of acetohydroxyacid synthase." Journal of Molecular Biology, vol. 263, pp. 359-368 (1996).

Hamilton A. J. et al., "Sense and antisense inactivation of fruit ripening genes in tomato." Current Topics in Microbiology Immunology, vol. 197, pp. 77-89 (1995).

Shaw, C. H. et al., "A functional map of the nopaline synthase promoter." Nucleic Acids Research, vol. 12, No. 20, pp. 7831-7846 (1984).

Comai, L. et al., "Novel and useful properties of a chimeric plant promoter combining CaMV 35S and MAS elements." Plant Molecular Biology, vol. 15, pp. 373-381 (1990).

Leisner, S. M. et al., "Structure of the octopine synthase upstream activator sequence." Proc. Natl. Acad. Sci. USA, vol. 85, pp. 2553-2557 (1988).

Odell, J. T. et al., "Identification of DNA sequences required for activity of the cauliflower mosaic virus 35S promoter." Nature, vol. 313, No. 28, pp. 810-812 (1985).

Battraw, M. J. et al., "Histochemical analysis of CaMV 35S promoter-β-glucuronidase gene expression in transgenic rice plants." Plant Molecular Biology, vol. 15, pp. 527-538 (1990).

Benfey, P. N. et al., "Tissue-specific expression from CaMV 35S enhancer subdomains in early stages of plant development." The EMBO Journal, vol. 9, No. 6, pp. 1677-1684 (1990).

Atanassova, R. et al., "Functional analysis of the promoter region of a maize (*Zea mays* L.) H3 histone gene in transgenic *Arabidopsis thaliana*." Plant Molecular Biology, vol. 37, pp. 275-285 (1998).

Holtorf, S. et al., "Comparison of different constitutive and inducible promoters for the overexpression of transgenes in *Arabidopsis thaliana*." Plant Molecular Biology, vol. 29, pp. 637-646 (1995).

Jefferson, R. A. et al., "GUS fusions: β-glucuronidase as a sensitive and versatile gene fusion marker in higher plants." The EMBO Journal, vol. 6, No. 13, pp. 3901-3907 (1987).

Al-Kaff, N. S. et al., "Plants rendered herbicide-susceptible by cauliflower mosaic virus-elicited suppression of a 35S promoter-regulated transgene." Nature Biotechnology, vol. 18, pp. 995-999 (2000).

Schenk, P. M. et al., "A promoter from sugarcane bacilliform badnavirus drives transgene expression in banana and other monocot and dicot plants." Plant Molecular Biology, vol. 39, pp. 1221-1230 (1999).

Ho, M. et al., "Cauliflower mosaic viral promoter—a recipe for disaster?" Microbial Ecology in Health and Disease, vol. 11, pp. 194-197 (1999).

Cummins J. et al., "Hazardous CaMV promoter?" Nature Biotechnology, vol. 18, p. 363 (2000).

Callis, J. et al., "Ubiquitin extension proteins of *Arabidopsis thaliana*." Journal of Biological Chemistry, vol. 265, No. 21, pp. 12486-12493 (1990).

Christensen, A. H. et al., "Ubiquitin promoter-based vectors for high-level expression of selectable and/or screenable marker genes in monocotyledonous plants." Transgenic Research, vol. 5, pp. 213-218 (1996).

McElroy, D. et al., "Construction of expression vectors based on the rice actin 1 (*Act* 1) 5' region for use in monocot transformation." Mol. Gen. Genet., vol. 231, pp. 150-160 (1991).

Stockhaus, J. et al., "Correlation of the expression of the nuclear photosynthetic gene ST-LS1 with the presence of chloroplats." The EMBO Journal, vol. 8, No. 9, pp. 2445-2451 (1989).

Oelmüller, R. et al., "Characterization of the promoter from the single-copy gene encoding ferredoxin—$NADP^+$—oxidoreductase from spinach." Mol. Gen. Genet., vol. 237, pp. 261-272 (1993).

Baerson, S. R. et al., "Developmental regulation of an acyl carrier protein gene promoter in vegetative and reproductive tissues." Plant Molecular Biology, vol. 22, pp. 255-267 (1993).

Broglie, R. et al., "Light-regulated expression of a pea ribulose-1,5-bisphosphate carboxylase small subunit gene in transformed plant cells." Science, vol. 224, pp. 838-843 (1984).

Atanassova, R. et al., "A 126 bp fragment of a plant histone gene promoter confers preferential expression in meristems of transgenic *Arabidopsis*." The Plant Journal, vol. 2, No. 3, pp. 291-300 (1992).

Guerrero, F. D. et al., "Promoter sequences from a maize pollen-specific gene direct tissue-specific transcription in tobacco." Mol. Gen. Genet., vol. 224, pp. 161-168 (1990).

Stalberg, K. et al., "Deletion analysis of a 2S seed storage protein promoter of *Brassica napus* in transgenic tobacco." Plant Molecular Biology, vol. 23, pp. 671-683 (1993).

Suzuki, H. et al., "Deletion analysis and localization of SbPRP1, a soybean cell wall protein gene, in roots of transgenic tobacco and cowpea." Plant Molecular Biology, vol. 21, pp. 109-119 (1993).

Bogusz, D. et al., "Nonlegume hemoglobin genes retain organ-specific expression in heterologous transgenic plants." The Plant Cell, vol. 2, pp. 633-641 (1990).

Bustos, M. M. et al., "Regulation of β-glucuronidase expression in transgenic tobacco plants by an A/T-rich, cis-acting sequence found upstream of a french bean β-phaseolin gene." The Plant Cell, vol. 1, pp. 839-853 (1989).

Josefsson, L. et al., "Structure of a gene encoding the 1.7 S storage protein, napin, from *Brassica napus*." Journal of Biological Chemistry, vol. 262, No. 25, pp. 12196-12201 (1987).

Shirsat, A. et al., "Sequences responsible for the tissue specific promoter activity of a pea legumin gene in tobacco." Mol. Gen. Genet., vol. 215, pp. 326-331 (1989).

Bäumlein, H. et al., "A novel seed protein gene from *Vicia faba* is developmentally regulated in transgenic tobacco and *Arabidopsis* plants." Mol. Gen. Genet., vol. 225, pp. 459-467 (1991).

Stalberg; K. et al., "Disruption of an overlapping E-box/ABRE motif abolished high transcription of the *nap* A storage-protein promoter in transgenic *Brassica napus* seeds." Planta, vol. 199, pp. 515-519 (1996).

Bäumlein, H. et al., "Upstream sequences regulating legumin gene expression in heterologous transgenic plants." Mol. Gen. Genet., vol. 225, pp. 121-128 (1991).

Elletström, M., et al., "Functional Dissection of a Napin Gene Promoter: Identification of Promoter Elements Required for Embryo and Endosperm-Specific Transcription", Plant Molecular Biology, vol. 32, (1996), pp. 1019-1027.

Altpeter, F., et al., "Increased Insect Resistance in Transgenic Wheat Stably Expressing Trypsin Inhibitor CMe", Molecular Breeding, vol. 5, (1999), pp. 53-63.

Murata, N., et al., "Genetically Engineered Alteration in the Chilling Sensitivity of Plants", Nature, vol. 356, (1992), pp. 710-713.

\* cited by examiner

Figure 1: Expression vector
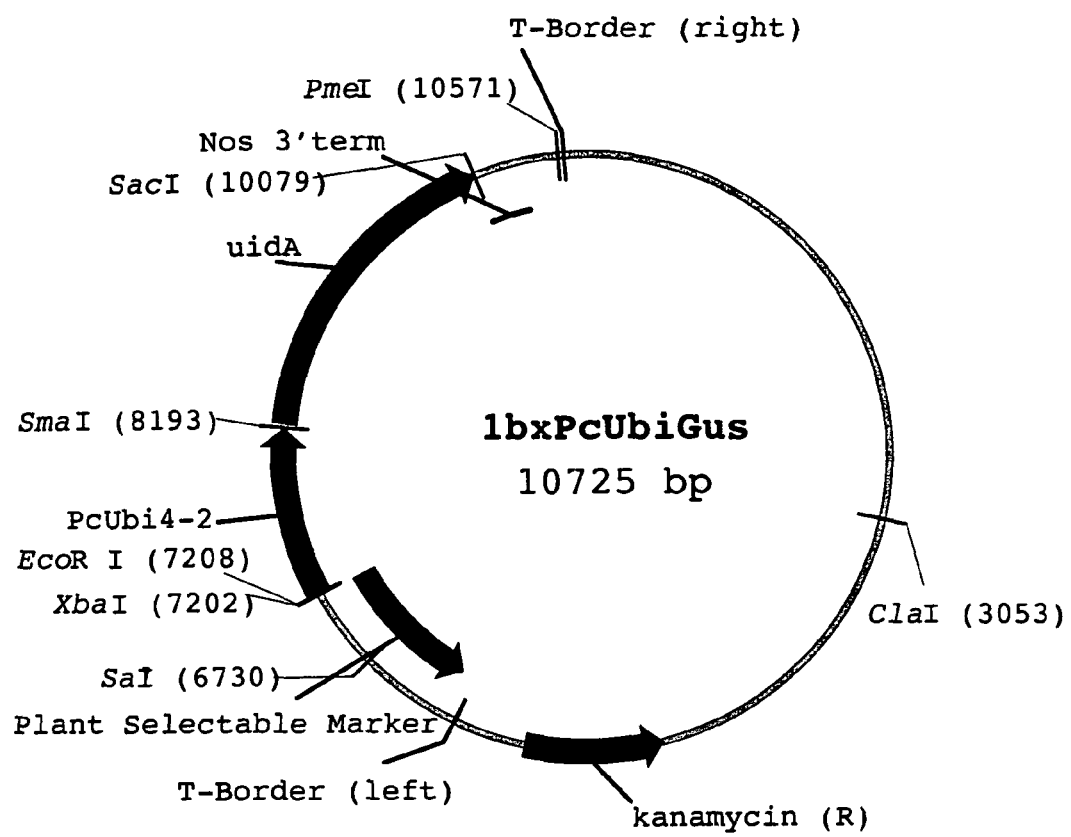

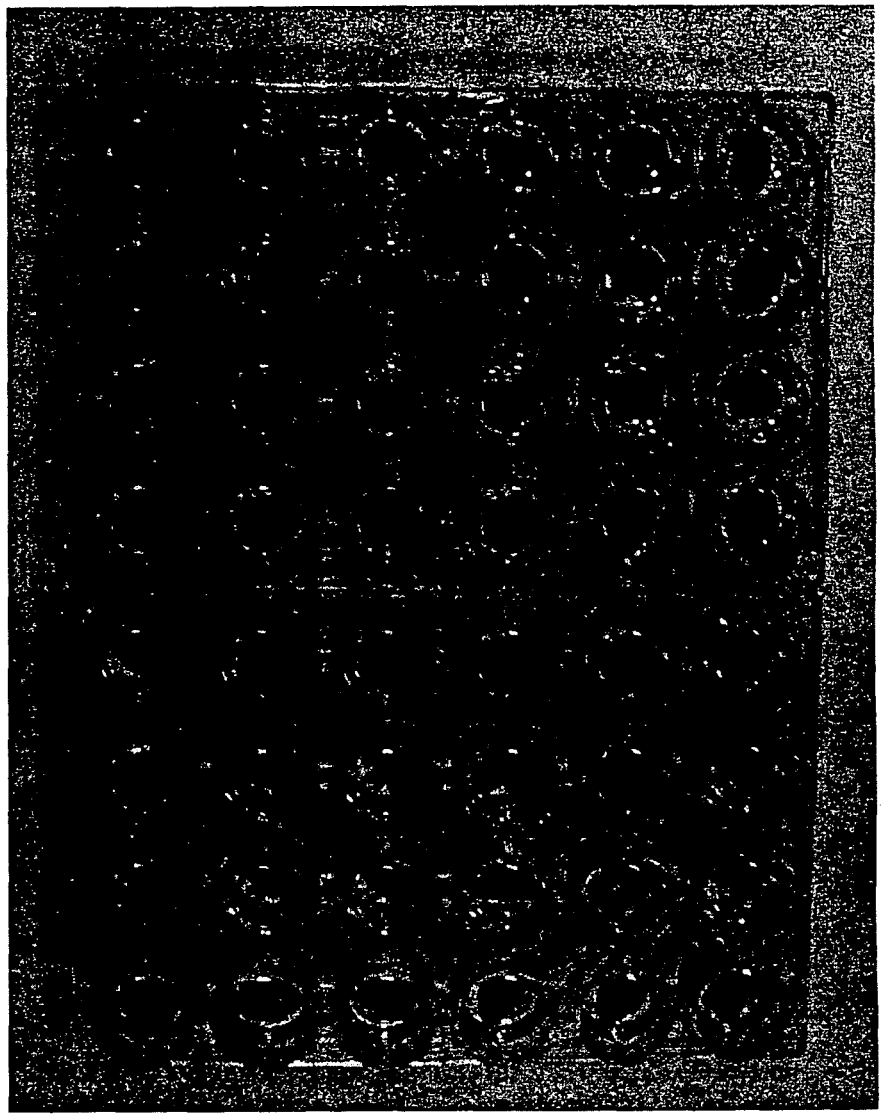
Figure 2: GUS staining of leaves of independent transgenic C24 Arabidopsis plants containing the Gus gene under the control of the PcUbi4-2 *P.crispum* promoter.

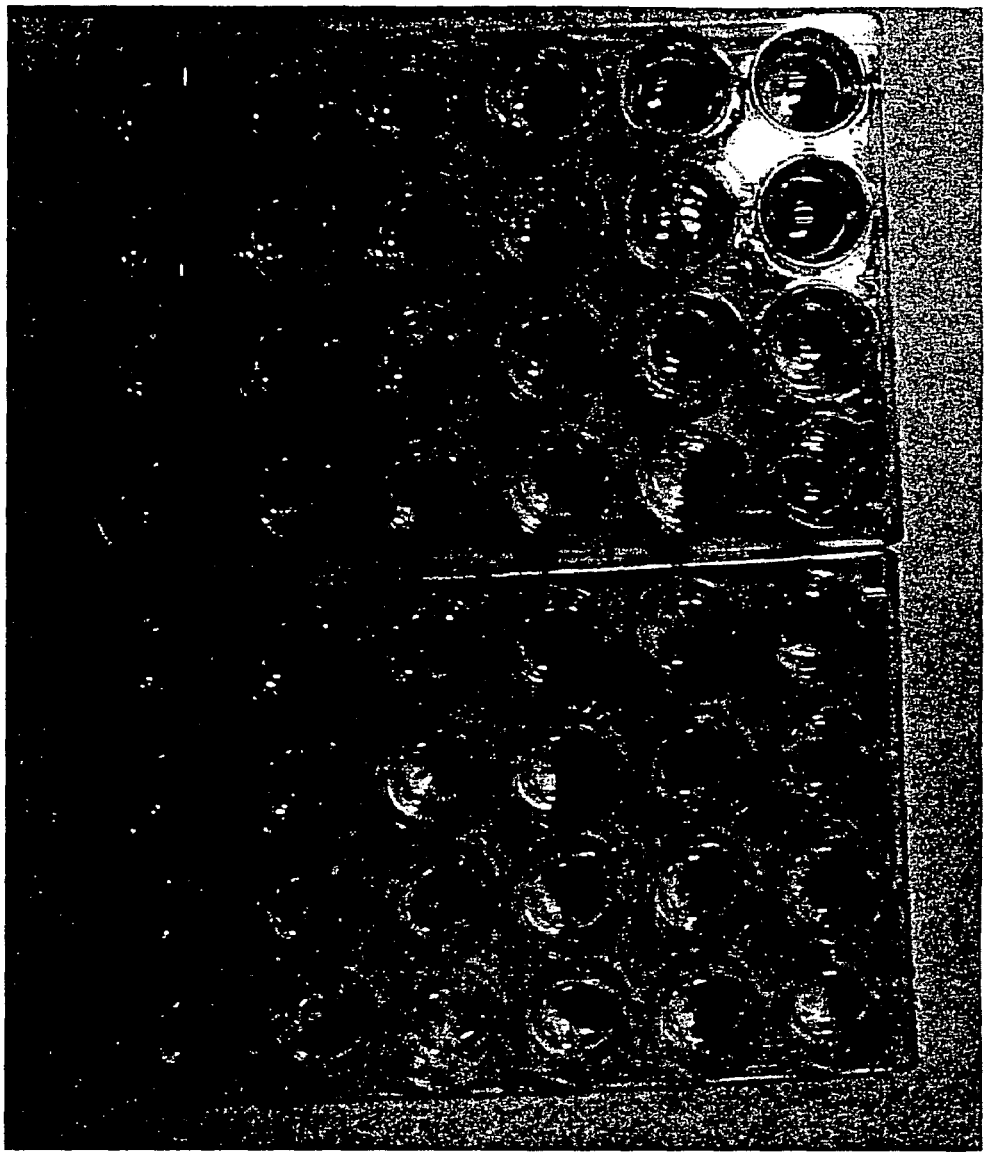
Figure 3: GUS staining of leaves of independent transgenic C24 Arabidopsis plants containing the Gus gene under the control of the d35S promoter.

Figure 4: GUS staining of the bud of a transgenic C24 Arabidopsis plant containing the Gus gene under the control of the Pc-Ubi4-2 *P.crispum* promoter.

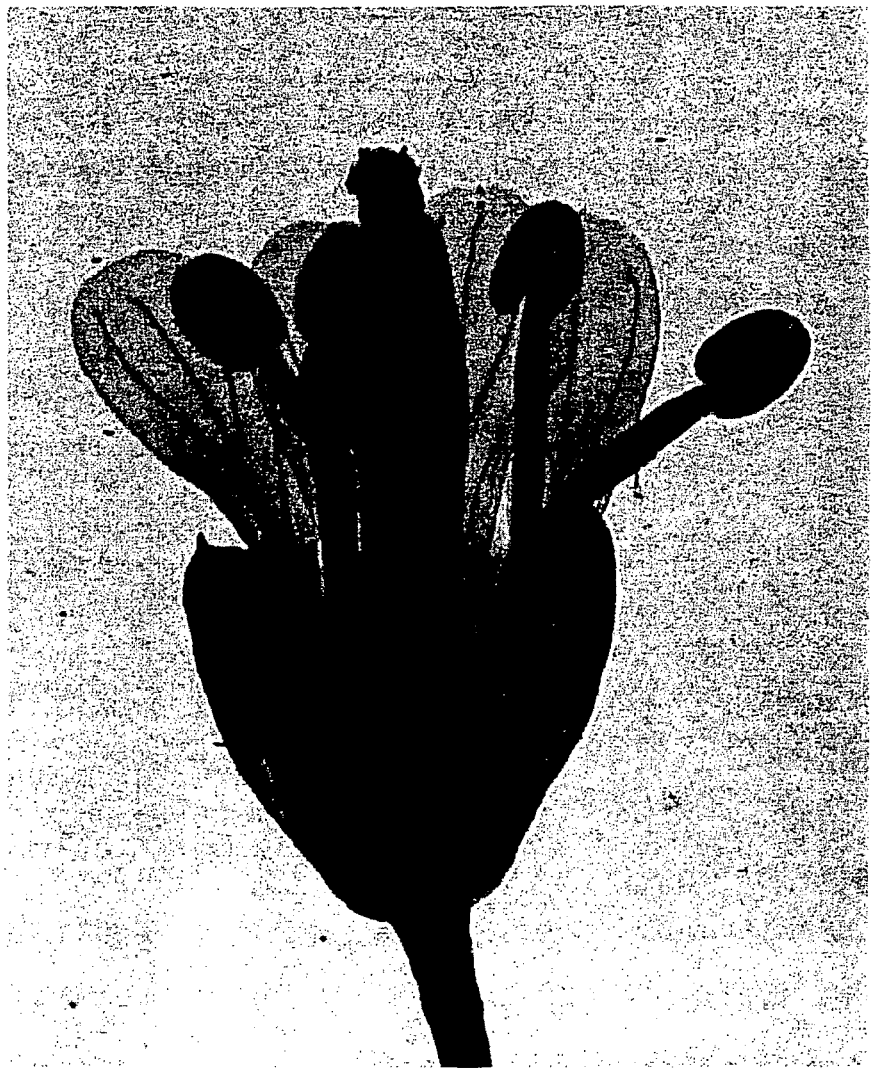
Figure 5: GUS staining of the flower of a transgenic C24 Arabidopsis plant containing the Gus gene under the control of the Pc-Ubi4-2 *P.crispum* promoter

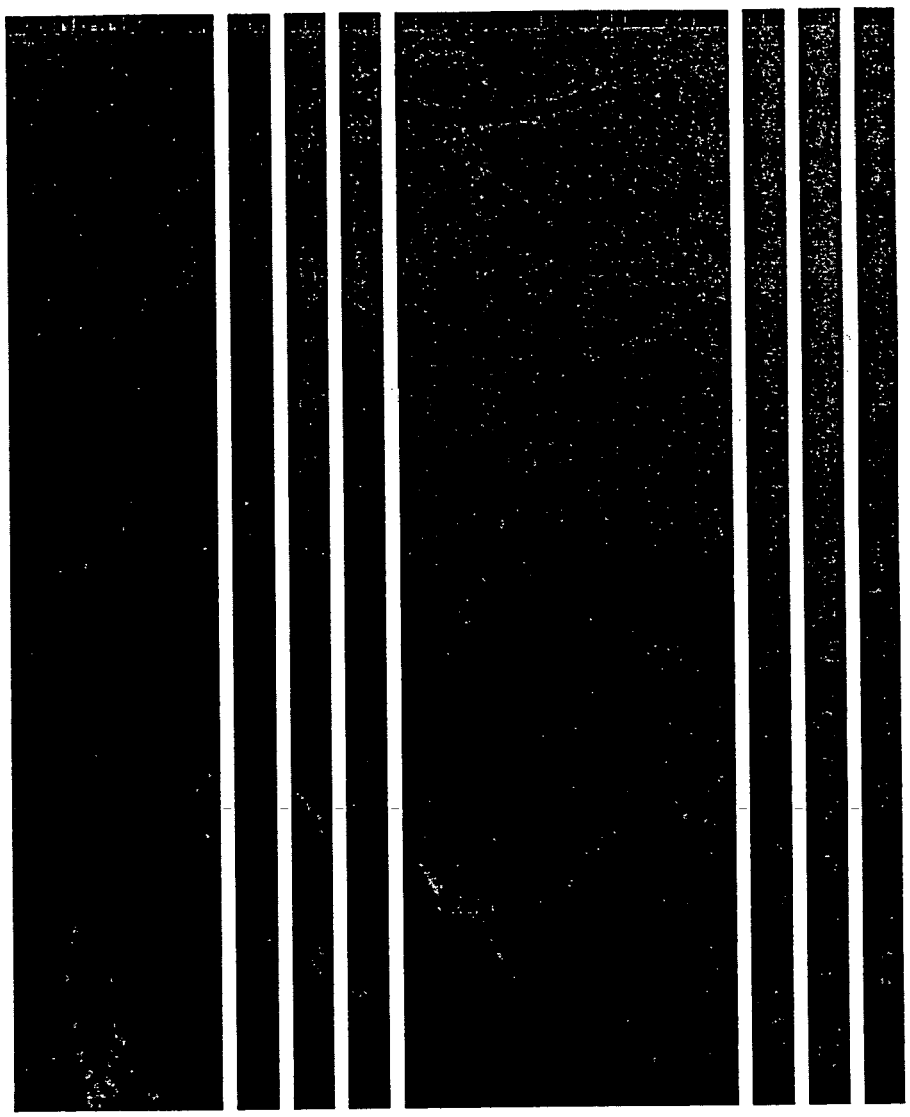
Figure 6: GUS staining of the root of a transgenic C24 Arabidopsis plant containing the Gus gene under the control of the Pc-Ubi4-2 P.crispum promoter

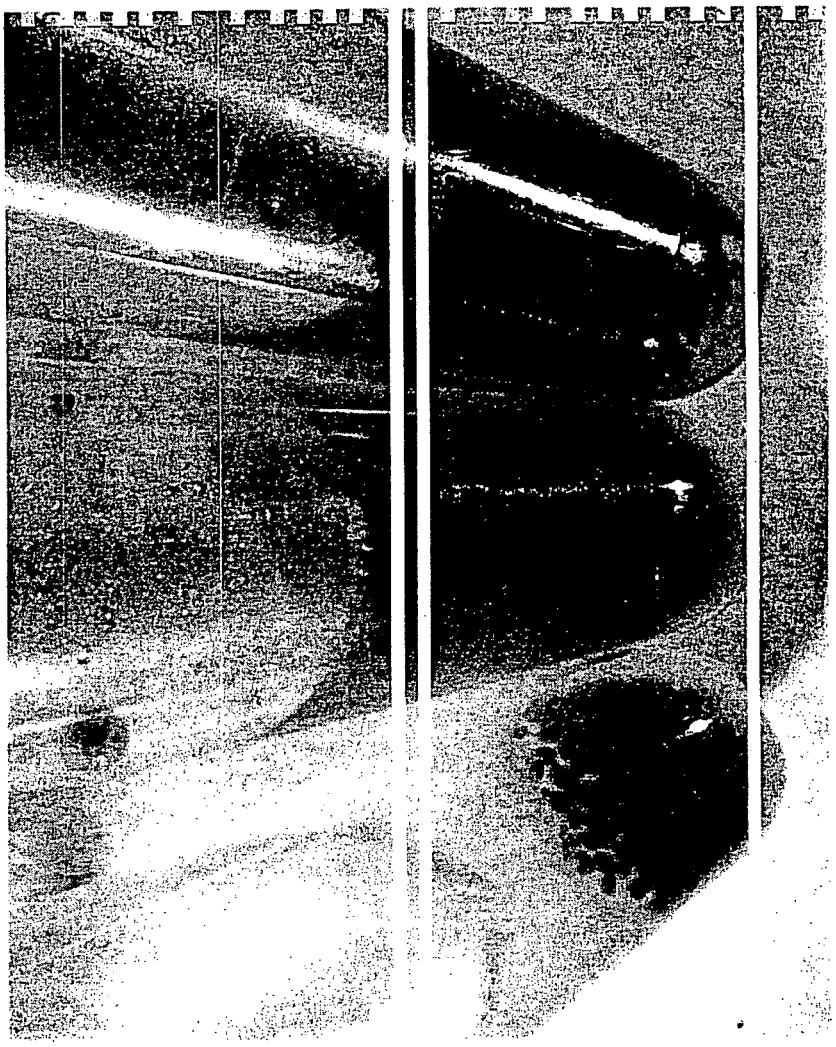
Figure 7: GUS staining of seeds of transgenic C24 Arabidopsis plants containing the Gus gene under the control of the *P. crispum* Pc-Ubi4-2 promotor (middle and right) or under the control of the d35S promotors (left).

Figure 8: Sequence of PcUbi4-2.

GAATTCGAATCCAAAAATTACGGATATGAATATAGGCATATCCGTATCCGAATTATCCGTT

TGACAGCTAGCAACGATTGTACAATTGCTTCTTTAAAAAAGGAAGAAAGAAAGAAAGAAAA

GAATCAACATCAGCGTT AACAAAC GGCCCCGTTACGGCCCAAACGGTCATATAGAGTAACG

GCGTTAAGCGTTGAAAGACTCCTATCGAAATACGTAACCGCAAACGTGTCATAGTCAGATC

CCCTCTTCCTTCACCGCCT CAAACAC AAAATAATCTTCTACAGCC TATATATA CAACCCC

CCCTTCTATCTCTCCTTTCTCACAATTCATCATCTTTCTTTCTCTACCCCCAATTTTAAGA

AATCCTCTCTTCTCCTCTTCATTTTCAAGGTAAATCTCTCTCTCTCTCTCTCTCTGTTA

TTCCTTGTTTTAATTAGGTATGTATTATTGCTA GTTTGTT AATCTGCTTATCTTATGTATG
                                   CAAACAA

CCTTATGTGAATATCTTTATCTTGTTCATCTCATCCGTTTAGAAGCTATAAATTTGTTGAT

TTGACTGTGTATCTACACGTGGTTATGTTTATATCTAATCAGATATGAATTTCTTCATATT

GTTGCGTTTGTGTGTACCAATCCGAAATCGTTGATTTTTTTCATTTAATCGTGTAGCTAAT

TGTACGTATACATATGGATCTACGTATCAATTGTTCATCTGTT GTGTTTC TATGTATACA
                                             CACAAAC

GATCTGAAAACATCACTTCTCTCATCTGATTGTGTTGTTACATACATAGATATAGATCTGT

TATATCATTTTTTTATTAATTGTGTATATATATATGTGCATAGATCTGGATTACATGATTG

TGATTATTTACATGATTTTGTTATTTACGTATGTATATATGTAGATCTGGACTTTTTGGAG

TTGTTGACTTGATTGTATTTGTGTGTGTATATGTGTGTTCTGATCTTGATATGTTATGTAT

GTGCAG

 Transcription start 327

 Intron

 annotated HSE

SEQUENCE LISTING

```
<160> NUMBER OF SEQ ID NOS: 29

<210> SEQ ID NO 1
<211> LENGTH: 982
<212> TYPE: DNA
<213> ORGANISM: Petroselinum crispum
<220> FEATURE:
<221> NAME/KEY: promoter
<222> LOCATION: (1)..(982)
<223> OTHER INFORMATION: Petroselinum promoter

<400> SEQUENCE: 1
gaattcgaat ccaaaaatta cggatatgaa tataggcata tccgtatccg aattatccgt     60
ttgacagcta gcaacgattg tacaattgct tctttaaaaa aggaagaaag aaagaaagaa    120
```

```
aagaatcaac atcagcgtta acaaacggcc ccgttacggc ccaaacggtc atatagagta    180
acggcgttaa gcgttgaaag actcctatcg aaatacgtaa ccgcaaacgt gtcatagtca    240 gatccctct tccttcaccg cctcaaacac aaaaataatc ttctacagcc tatatataca    300
accccccctt ctatctctcc tttctcacaa ttcatcatct ttctttctct accccaatt    360 ttaagaaatc ctctcttctc ctcttcattt tcaaggtaaa tctctctctc tctctctctc    420
tctgttattc cttgttttaa ttaggtatgt attattgcta gtttgttaat ctgcttatct    480
tatgtatgcc ttatgtgaat atctttatct tgttcatctc atccgtttag aagctataaa    540
tttgttgatt tgactgtgta tctacacgtg gttatgttta tatctaatca gatatgaatt    600
tcttcatatt gttgcgtttg tgtgtaccaa tccgaaatcg ttgattttt tcatttaatc    660 gtgtagctaa ttgtacgtat acatatggat ctacgtatca attgttcatc tgtttgtgtt    720
tgtatgtata cagatctgaa aacatcactt ctctcatctg attgtgttgt tacatacata    780
gatatagatc tgttatatca ttttttatt aattgtgtat atatatatgt gcatagatct    840
ggattacatg attgtgatta tttacatgat tttgttattt acgtatgtat atatgtagat    900
ctggactttt tggagttgtt gacttgattg tatttgtgtg tgtatatgtg tgttctgatc    960
ttgatatgtt atgtatgtgc ag                                            982
```

```
<210> SEQ ID NO 2
<211> LENGTH: 3598
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(3598)
<223> OTHER INFORMATION: Sequence is a plant promoter-terminator
      expression cassette in the pUC19 vector

<400> SEQUENCE: 2
```

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cggcgcgccg agctcctcga    420
gcaaatttac acattgccac taaacgtcta aacccttgta atttgttttt gttttactat    480
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taattttca    840 agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
```

```
atataatgag gattttgcaa tactttcatt catacacact cactaagttt tacacgatta    1080
taatttcttc atagccagcc caccgcggtg ggcggccgcc tgcagtctag aaggcctcct    1140
gctttaatga gatatgcgag acgcctatga tcgcatgata tttgctttca attctgttgt    1200
gcacgttgta aaaacctga gcatgtgtag ctcagatcct taccgccggt ttcggttcat    1260
tctaatgaat atatcacccg ttactatcgt attttatga ataatattct ccgttcaatt    1320
tactgattgt ccgtcgacga attcgagctc ggcgcgccaa gcttggcgta atcatggtca    1380
tagctgtttc ctgtgtgaaa ttgttatccg ctcacaattc cacacaacat acgagccgga    1440
agcataaagt gtaaagcctg gggtgcctaa tgagtgagct aactcacatt aattgcgttg    1500
cgctcactgc ccgctttcca gtcgggaaac ctgtcgtgcc agctgcatta atgaatcggc    1560
caacgcgcgg ggagaggcgg tttgcgtatt gggcgctctt ccgcttcctc gctcactgac    1620
tcgctgcgct cggtcgttcg gctgcggcga gcggtatcag ctcactcaaa ggcggtaata    1680
cggttatcca cagaatcagg ggataacgca ggaaagaaca tgtgagcaaa aggccagcaa    1740
aaggccagga accgtaaaaa ggccgcgttg ctggcgtttt tccataggct ccgcccccct    1800
gacgagcatc acaaaaatcg acgctcaagt cagaggtggc gaaacccgac aggactataa    1860
agataccagg cgtttccccc tggaagctcc ctcgtgcgct ctcctgttcc gaccctgccg    1920
cttaccggat acctgtccgc ctttctccct tcgggaagcg tggcgctttc tcatagctca    1980
cgctgtaggt atctcagttc ggtgtaggtc gttcgctcca agctgggctg tgtgcacgaa    2040
ccccccgttc agcccgaccg ctgcgcctta tccggtaact atcgtcttga gtccaacccg    2100
gtaagacacg acttatcgcc actggcagca gccactggta acaggattag cagagcgagg    2160
tatgtaggcg gtgctacaga gttcttgaag tggtggccta actacggcta cactagaagg    2220
acagtatttg gtatctgcgc tctgctgaag ccagttacct tcggaaaaag agttggtagc    2280
tcttgatccg gcaaacaaac caccgctggt agcggtggtt ttttgtttg caagcagcag    2340
attacgcgca gaaaaaagg atcctttga tcttttctac ggggtctgac    2400
gctcagtgga acgaaaactc acgttaaggg attttggtca tgagattatc aaaaaggatc    2460
ttcacctaga tcccttttaaa ttaaaaatga agttttaaat caatctaaag tatatatgag    2520
taaacttggt ctgacagtta ccaatgctta atcagtgagg cacctatctc agcgatctgt    2580
ctatttcgtt catccatagt tgcctgactc cccgtcgtgt agataactac gatacgggag    2640
ggcttaccat ctggccccag tgctgcaatg ataccgcgag acccacgctc accggctcca    2700
gatttatcag caataaacca gccagccgga agggccgagc gcagaagtgg tcctgcaact    2760
ttatccgcct ccatccagtc tattaattgt tgccgggaag ctagagtaag tagttcgcca    2820
gttaatagtt tgcgcaacgt tgttgccatt gctacaggca tcgtggtgtc acgctcgtcg    2880
tttggtatgg cttcattcag ctccggttcc caacgatcaa ggcgagttac atgatccccc    2940
atgttgtgca aaaaagcggt tagctccttc ggtcctccga tcgttgtcag aagtaagttg    3000
gccgcagtgt tatcactcat ggttatggca gcactgcata attctcttac tgtcatgcca    3060
tccgtaagat gcttttctgt gactggtgag tactcaacca agtcattctg agaatagtgt    3120
atgcggcgac cgagttgctc ttgcccggcg tcaatacggg ataataccgc gccacatagc    3180
agaactttaa aagtgctcat cattggaaaa cgttcttcgg ggcgaaaact ctcaaggatc    3240
ttaccgctgt tgagatccag ttcgatgtaa cccactcgtg cacccaactg atcttcagca    3300
tcttttactt tcaccagcgt ttctgggtga gcaaaaacag gaaggcaaaa tgccgcaaaa    3360
aagggaataa gggcgacacg gaaatgttga atactcatac tcttcctttt tcaatattat    3420
```

| | | |
|---|---|---|
| tgaagcattt atcagggtta ttgtctcatg agcggataca tatttgaatg tatttagaaa | 3480 | |
| aataaacaaa tagggttcc gcgcacattt ccccgaaaag tgccacctga cgtctaagaa | 3540 | |
| accattatta tcatgacatt aacctataaa aataggcgta tcacgaggcc ctttcgtc | 3598 | |

<210> SEQ ID NO 3
<211> LENGTH: 3590
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(3590)
<223> OTHER INFORMATION: Sequence is a plant promoter-terminator expression cassette in the pUC19 vector

<400> SEQUENCE: 3

| | | |
|---|---|---|
| tcgcgcgttt cggtgatgac ggtgaaaacc tctgacacat gcagctcccg gagacggtca | 60 | |
| cagcttgtct gtaagcggat gccgggagca gacaagcccg tcagggcgcg tcagcgggtg | 120 | |
| ttggcgggtg tcggggctgg cttaactatg cggcatcaga gcagattgta ctgagagtgc | 180 | |
| accatatgcg gtgtgaaata ccgcacagat gcgtaaggag aaaataccgc atcaggcgcc | 240 | |
| attcgccatt caggctgcgc aactgttggg aagggcgatc ggtgcgggcc tcttcgctat | 300 | |
| tacgccagct ggcgaaaggg ggatgtgctg caaggcgatt aagttgggta acgccagggt | 360 | |
| tttcccagtc acgacgttgt aaaacgacgg ccagtgaatt cggcgcgccg agctcctcga | 420 | |
| gcaaatttac acattgccac taaacgtcta aaccccttgta atttgttttt gttttactat | 480 | |
| gtgtgttatg tatttgattt gcgataaatt tttatatttg gtactaaatt tataacacct | 540 | |
| tttatgctaa cgtttgccaa cacttagcaa tttgcaagtt gattaattga ttctaaatta | 600 | |
| ttttttgtctt ctaaatacat atactaatca actggaaatg taaatatttg ctaatatttc | 660 | |
| tactatagga gaattaaagt gagtgaatat ggtaccacaa ggtttggaga tttaattgtt | 720 | |
| gcaatgctgc atggatggca tatacaccaa acattcaata attcttgagg ataataatgg | 780 | |
| taccacacaa gatttgaggt gcatgaacgt cacgtggaca aaaggtttag taattttttca | 840 | |
| agacaacaat gttaccacac acaagttttg aggtgcatgc atggatgccc tgtggaaagt | 900 | |
| ttaaaaatat tttggaaatg atttgcatgg aagccatgtg taaaaccatg acatccactt | 960 | |
| ggaggatgca ataatgaaga aaactacaaa tttacatgca actagttatg catgtagtct | 1020 | |
| atataatgag gattttgcaa tactttcatt catacacact cactaagttt tacacgatta | 1080 | |
| taatttcttc atagccagcg gatccgatat cgggcccgct agcgttaacc ctgctttaat | 1140 | |
| gagatatgcg agacgcctat gatcgcatga tatttgcttt caattctgtt gtgcacgttg | 1200 | |
| taaaaaacct gagcatgtgt agctcagatc cttaccgccg gtttcggttc attctaatga | 1260 | |
| atatatcacc cgttactatc gtattttat gaataatatt ctccgttcaa tttactgatt | 1320 | |
| gtccgtcgac gaattcgagc tcggcgcgcc aagcttggcg taatcatggt catagctgtt | 1380 | |
| tcctgtgtga aattgttatc cgctcacaat tccacacaac atacgagccg gaagcataaa | 1440 | |
| gtgtaaagcc tggggtgcct aatgagtgag ctaactcaca ttaattgcgt tgcgctcact | 1500 | |
| gcccgctttc cagtcgggaa acctgtcgtg ccagctgcat taatgaatcg gccaacgcgc | 1560 | |
| ggggagaggc ggtttgcgta ttgggcgctc ttccgcttcc tcgctcactg actcgctgcg | 1620 | |
| ctcggtcgtt cggctgcggc gagcggtatc agctcactca aaggcggtaa tacggttatc | 1680 | |
| cacagaatca ggggataacg caggaaagaa catgtgagca aaaggccagc aaaaggccag | 1740 | |
| gaaccgtaaa aaggccgcgt tgctggcgtt tttccatagg ctccgccccc ctgacgagca | 1800 | |

-continued

| | |
|---|---|
| tcacaaaaat cgacgctcaa gtcagaggtg gcgaaacccg acaggactat aaagatacca | 1860 |
| ggcgtttccc cctggaagct ccctcgtgcg ctctcctgtt ccgaccctgc cgcttaccgg | 1920 |
| atacctgtcc gcctttctcc cttcgggaag cgtggcgctt tctcatagct cacgctgtag | 1980 |
| gtatctcagt tcggtgtagg tcgttcgctc caagctgggc tgtgtgcacg aaccccccgt | 2040 |
| tcagcccgac cgctgcgcct tatccggtaa ctatcgtctt gagtccaacc cggtaagaca | 2100 |
| cgacttatcg ccactggcag cagccactgg taacaggatt agcagagcga ggtatgtagg | 2160 |
| cggtgctaca gagttcttga agtggtggcc taactacggc tacactagaa ggacagtatt | 2220 |
| tggtatctgc gctctgctga agccagttac cttcggaaaa agagttggta gctcttgatc | 2280 |
| cggcaaacaa accaccgctg gtagcggtgg ttttttttgtt tgcaagcagc agattacgcg | 2340 |
| cagaaaaaaa ggatctcaag aagatccttt gatcttttct acggggtctg acgctcagtg | 2400 |
| gaacgaaaac tcacgttaag ggattttggt catgagatta tcaaaaagga tcttcaccta | 2460 |
| gatccttta aattaaaaat gaagttttaa atcaatctaa agtatatatg agtaaacttg | 2520 |
| gtctgacagt taccaatgct taatcagtga ggcacctatc tcagcgatct gtctatttcg | 2580 |
| ttcatccata gttgcctgac tccccgtcgt gtagataact acgatacggg agggcttacc | 2640 |
| atctggcccc agtgctgcaa tgataccgcg agacccacgc tcaccggctc cagatttatc | 2700 |
| agcaataaac cagccagccg gaagggccga gcgcagaagt ggtcctgcaa ctttatccgc | 2760 |
| ctccatccag tctattaatt gttgccggga agctagagta agtagttcgc cagttaatag | 2820 |
| tttgcgcaac gttgttgcca ttgctacagg catcgtggtg tcacgctcgt cgtttggtat | 2880 |
| ggcttcattc agctccggtt cccaacgatc aaggcgagtt acatgatccc ccatgttgtg | 2940 |
| caaaaaagcg gttagctcct tcggtcctcc gatcgttgtc agaagtaagt tggccgcagt | 3000 |
| gttatcactc atggttatgg cagcactgca taattctctt actgtcatgc catccgtaag | 3060 |
| atgcttttct gtgactggtg agtactcaac caagtcattc tgagaatagt gtatgcggcg | 3120 |
| accgagttgc tcttgcccgg cgtcaatacg ggataatacc gcgccacata gcagaacttt | 3180 |
| aaaagtgctc atcattggaa aacgttcttc ggggcgaaaa ctctcaagga tcttaccgct | 3240 |
| gttgagatcc agttcgatgt aacccactcg tgcacccaac tgatcttcag catctttac | 3300 |
| tttcaccagc gtttctgggt gagcaaaaac aggaaggcaa aatgccgcaa aaagggaat | 3360 |
| aagggcgaca cggaaatgtt gaatactcat actcttcctt tttcaatatt attgaagcat | 3420 |
| ttatcagggt tattgtctca tgagcggata catatttgaa tgtatttaga aaataaaca | 3480 |
| aatagggtt ccgcgcacat ttccccgaaa agtgccacct gacgtctaag aaaccattat | 3540 |
| tatcatgaca ttaacctata aaataggcg tatcacgagg ccctttcgtc | 3590 |

<210> SEQ ID NO 4
<211> LENGTH: 3584
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(3584)
<223> OTHER INFORMATION: Sequence is a plant promoter-terminator
      expression cassette in the pUC19 vector

<400> SEQUENCE: 4

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cggcgcgccg agctcctcga    420
gcaaatttac acattccac taaacgtcta aacccttgta atttgttttt gttttactat     480
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
tactatagga gaattaaagt gagtgaatat ggtaccacaa ggtttggaga tttaattgtt    720
gcaatgctgc atggatggca tataccaa acattcaata attcttgagg ataataatgg      780
taccacacaa gatttgaggt gcatgaacgt cacgtggaca aaaggtttag taattttttca   840
agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagca gatctgccgg catcgatccc gggccatggc ctgctttaat   1140
gagatatgcg agacgcctat gatcgcatga tatttgcttt caattctgtt gtgcacgttg   1200
taaaaaacct gagcatgtgt agctcagatc cttaccgccg gtttcggttc attctaatga   1260
atatatcacc cgttactatc gtatttttat gaataatatt ctccgttcaa tttactgatt   1320
gtccgtcgac gagctcggcg cgccaagctt ggcgtaatca tggtcatagc tgtttcctgt   1380
gtgaaattgt tatccgctca caattccaca caacatacga gccggaagca taaagtgtaa   1440
agcctggggt gcctaatgag tgagctaact cacattaatt gcgttgcgct cactgcccgc   1500
tttccagtcg ggaaacctgt cgtgccagct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgttttttcca taggctccgc ccccctgacg agcatcacaa   1800
aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcat agctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
```

-continued

| | |
|---|---|
| cagttaccaa tgcttaatca gtgaggcacc tatctcagcg atctgtctat ttcgttcatc | 2580 |
| catagttgcc tgactcccg tcgtgtagat aactacgata cgggagggct taccatctgg | 2640 |
| ccccagtgct gcaatgatac cgcgagaccc acgctcaccg gctccagatt tatcagcaat | 2700 |
| aaaccagcca gccggaaggg ccgagcgcag aagtggtcct gcaactttat ccgcctccat | 2760 |
| ccagtctatt aattgttgcc gggaagctag agtaagtagt tcgccagtta atagtttgcg | 2820 |
| caacgttgtt gccattgcta caggcatcgt ggtgtcacgc tcgtcgtttg gtatggcttc | 2880 |
| attcagctcc ggttcccaac gatcaaggcg agttacatga tcccccatgt tgtgcaaaaa | 2940 |
| agcggttagc tccttcggtc ctccgatcgt tgtcagaagt aagttggccg cagtgttatc | 3000 |
| actcatggtt atggcagcac tgcataattc tcttactgtc atgccatccg taagatgctt | 3060 |
| ttctgtgact ggtgagtact caaccaagtc attctgagaa tagtgtatgc ggcgaccgag | 3120 |
| ttgctcttgc ccggcgtcaa tacgggataa taccgcgcca catagcagaa ctttaaaagt | 3180 |
| gctcatcatt ggaaaacgtt cttcggggcg aaaactctca aggatcttac cgctgttgag | 3240 |
| atccagttcg atgtaaccca ctcgtgcacc caactgatct tcagcatctt ttactttcac | 3300 |
| cagcgtttct gggtgagcaa aaacaggaag gcaaaatgcc gcaaaaaagg gaataagggc | 3360 |
| gacacggaaa tgttgaatac tcatactctt cctttttcaa tattattgaa gcatttatca | 3420 |
| gggttattgt ctcatgagcg gatacatatt tgaatgtatt tagaaaaata aacaaatagg | 3480 |
| ggttccgcgc acatttcccc gaaaagtgcc acctgacgtc taagaaacca ttattatcat | 3540 |
| gacattaacc tataaaaata ggcgtatcac gaggcccttt cgtc | 3584 |

<210> SEQ ID NO 5
<211> LENGTH: 4507
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(4507)
<223> OTHER INFORMATION: Sequence is a plant promoter-terminator
      expression cassette in the pUC19 vector

<400> SEQUENCE: 5

| | |
|---|---|
| tcgcgcgttt cggtgatgac ggtgaaaacc tctgacacat gcagctcccg gagacggtca | 60 |
| cagcttgtct gtaagcggat gccggagcca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cggcgcgccg agctcctcga | 420 |
| gcaaatttac acattgccac taaacgtcta aacccttgta atttgttttt gttttactat | 480 |
| gtgtgttatg tatttgattt gcgataaatt tttatatttg gtactaaatt tataacacct | 540 |
| tttatgctaa cgtttgccaa cacttagcaa tttgcaagtt gattaattga ttctaaatta | 600 |
| tttttgtctt ctaaatacat atactaatca actggaaatg taaatatttg ctaatatttc | 660 |
| tactatagga gaattaaagt gagtgaatat ggtaccacaa ggtttggaga tttaattgtt | 720 |
| gcaatgctgc atggatggca tatacaccaa acattcaata attcttgagg ataataatgg | 780 |
| taccacacaa gatttgaggt gcatgaacgt cacgtggaca aaaggtttag taattttca | 840 |
| agacaacaat gttaccacac acaagttttg aggtgcatgc atggatgccc tgtggaaagt | 900 |

```
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gatttttgcaa tactttcatt catacacact cactaagttt tacacgatta  1080
taatttcttc atagccagcc caccgcggtg ggcggccgcc tgcagtctag aaggcctcct   1140
gctttaatga gatatgcgag acgcctatga tcgcatgata tttgctttca attctgttgt   1200
gcacgttgta aaaacctga gcatgtgtag ctcagatcct taccgccggt ttcggttcat    1260
tctaatgaat atatcacccg ttactatcgt attttatga ataatattct ccgttcaatt    1320
tactgattgt ccgtcgagca aatttacaca ttgccactaa acgtctaaac ccttgtaatt   1380
tgttttgtt ttactatgtg tgttatgtat ttgatttgcg ataaatttt atatttggta     1440
ctaaatttat aacacctttt atgctaacgt ttgccaacac ttagcaattt gcaagttgat   1500
taattgattc taaattattt ttgtcttcta aatacatata ctaatcaact ggaaatgtaa   1560
atatttgcta atatttctac tataggagaa ttaaagtgag tgaatatggt accacaaggt   1620
ttggagattt aattgttgca atgctgcatg gatggcatat acaccaaaca ttcataatt    1680
cttgaggata ataatggtac cacacaagat ttgaggtgca tgaacgtcac gtggacaaaa   1740
ggtttagtaa tttttcaaga caacaatgtt accacacaca agttttgagg tgcatgcatg   1800
gatgccctgt ggaagtttta aaatattttt ggaaatgatt tgcatggaag ccatgtgtaa   1860
aaccatgaca tccacttgga ggatgcaata atgaagaaaa ctacaaattt acatgcaact   1920
agttatgcat gtagtctata taatgaggat tttgcaatac tttcattcat acacactcac   1980
taagttttac acgattataa tttcttcata gccagcggat ccgatatcgg gcccgctagc   2040
gttaaccctg ctttaatgag atatgcgaga cgcctatgat cgcatgatat ttgctttcaa   2100
ttctgttgtg cacgttgtaa aaacctgag catgtgtagc tcagatcctt accgccggtt    2160
tcggttcatt ctaatgaata tatcacccgt tactatcgta tttttatgaa taatattctc   2220
cgttcaattt actgattgtc cgtcgacgaa ttcgagctcg gcgcgccaag cttggcgtaa   2280
tcatggtcat agctgtttcc tgtgtgaaat tgttatccgc tcacaattcc acacaacata   2340
cgagccggaa gcataaagtg taaagcctgg ggtgcctaat gagtgagcta actcacatta   2400
attgcgttgc gctcactgcc cgcttttcag tcgggaaacc tgtcgtgcca gctgcattaa   2460
tgaatcggcc aacgcgcggg gagaggcggt ttgcgtattg ggcgctcttc cgcttcctcg   2520
ctcactgact cgctgcgctc ggtcgttcgg ctgcggcgag cggtatcagc tcactcaaag   2580
gcggtaatac ggttatccac agaatcaggg gataacgcag gaaagaacat gtgagcaaaa   2640
ggccagcaaa aggccaggaa ccgtaaaaag gccgcgttgc tggcgttttt ccataggctc   2700
cgcccccctg acgagcatca caaaaatcga cgctcaagtc agaggtggcg aaacccgaca   2760
ggactataaa gataccaggc gtttccccct ggaagctccc tcgtgcgctc tcctgttccg   2820
accctgccgc ttaccggata cctgtccgcc tttctccctt cgggaagcgt ggcgctttct   2880
catagctcac gctgtaggta tctcagttcg gtgtaggtcg ttcgctccaa gctgggctgt   2940
gtgcacgaac cccccgttca gcccgaccgc tgcgccttat ccggtaacta tcgtcttgag   3000
tccaacccgg taagacacga cttatcgcca ctggcagcag ccactggtaa caggattagc   3060
agagcgaggt atgtaggcgg tgctacagag ttcttgaagt ggtggcctaa ctacggctac   3120
actagaagga cagtatttgg tatctgcgct ctgctgaagc cagttacctt cggaaaaaga   3180
gttggtagct cttgatccgg caaacaaacc accgctggta gcggtggttt ttttgtttgc   3240
aagcagcaga ttacgcgcag aaaaaaagga tctcaagaag atcctttgat cttttctacg   3300
```

```
gggtctgacg ctcagtggaa cgaaaactca cgttaaggga ttttggtcat gagattatca   3360
aaaaggatct tcacctagat cctttttaaat taaaaatgaa gttttaaatc aatctaaagt   3420
atatatgagt aaacttggtc tgacagttac caatgcttaa tcagtgaggc acctatctca   3480
gcgatctgtc tatttcgttc atccatagtt gcctgactcc ccgtcgtgta gataactacg   3540
atacgggagg gcttaccatc tggccccagt gctgcaatga taccgcgaga cccacgctca   3600
ccggctccag atttatcagc aataaaccag ccagccggaa gggccgagcg cagaagtggt   3660
cctgcaactt tatccgcctc catccagtct attaattgtt gccgggaagc tagagtaagt   3720
agttcgccag ttaatagttt gcgcaacgtt gttgccattg ctacaggcat cgtggtgtca   3780
cgctcgtcgt ttggtatggc ttcattcagc tccggttccc aacgatcaag gcgagttaca   3840
tgatccccca tgttgtgcaa aaaagcggtt agctccttcg gtcctccgat cgttgtcaga   3900
agtaagttgg ccgcagtgtt atcactcatg gttatggcag cactgcataa ttctcttact   3960
gtcatgccat ccgtaagatg cttttctgtg actggtgagt actcaaccaa gtcattctga   4020
gaatagtgta tgcggcgacc gagttgctct tgcccggcgt caatacggga taataccgcg   4080
ccacatagca gaactttaaa agtgctcatc attggaaaac gttcttcggg gcgaaaactc   4140
tcaaggatct taccgctgtt gagatccagt tcgatgtaac ccactcgtgc acccaactga   4200
tcttcagcat cttttacttt caccagcgtt tctgggtgag caaaaacagg aaggcaaaat   4260
gccgcaaaaa agggaataag ggcgacacgg aaatgttgaa tactcatact cttccttttt   4320
caatattatt gaagcattta tcagggttat tgtctcatga gcggatacat atttgaatgt   4380
atttagaaaa ataaacaaat aggggttccg cgcacatttc cccgaaaagt gccacctgac   4440
gtctaagaaa ccattattat catgacatta acctataaaa ataggcgtat cacgaggccc   4500
tttcgtc                                                              4507

<210> SEQ ID NO 6
<211> LENGTH: 5410
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(5410)
<223> OTHER INFORMATION: Sequence is a plant promoter-terminator
      expression cassette in the pUC19 vector

<400> SEQUENCE: 6
ttttggaaat gatttgcatg gaagccatgt gtaaaaccat gacatccact tggaggatgc     60
aataatgaag aaaactacaa atttacatgc aactagttat gcatgtagtc tatataatga    120
ggattttgca atactttcat tcatacacac tcactaagtt ttacacgatt ataatttctt    180
catagccagc ggatccgata tcgggcccgc tagcgttaac cctgctttaa tgagatatgc    240
gagacgccta tgatcgcatg atatttgctt tcaattctgt tgtgcacgtt gtaaaaaacc    300
tgagcatgtg tagctcagat ccttaccgcc ggtttcggtt cattctaatg aatatatcac    360
ccgttactat cgtattttta tgaataatat tctccgttca atttactgat tgtccgtcga    420
gcaaatttac acattgccac taaacgtcta aacccttgta atttgttttt gttttactat    480
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
```

```
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taatttttca    840
agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagca gatctgccgg catcgatccc gggccatggc ctgctttaat   1140
gagatatgcg agacgcctat gatcgcatga tatttgcttt caattctgtt gtgcacgttg   1200
taaaaaacct gagcatgtgt agctcagatc cttaccgccg gtttcggttc attctaatga   1260
atatatcacc cgttactatc gtatttttat gaataatatt ctccgttcaa tttactgatt   1320
gtccgtcgac gagctcggcg cgccaagctt ggcgtaatca tggtcatagc tgtttcctgt   1380
gtgaaattgt tatccgctca caattccaca acatacga gccggaagca taaagtgtaa   1440 agcctgggt gcctaatgag tgagctaact cacattaatt gcgttgcgct cactgcccgc   1500
tttccagtcg ggaaacctgt cgtgccagct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgtttttcca taggctccgc cccctgacg agcatcacaa   1800 aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcat agctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
cagttaccaa tgcttaatca gtgaggcacc tatctcagcg atctgtctat ttcgttcatc   2580
catagttgcc tgactccccg tcgtgtagat aactacgata cgggagggct taccatctgg   2640
ccccagtgct gcaatgatac cgcgagaccc acgctcaccg gctccagatt tatcagcaat   2700
aaaccagcca gccggaaggg ccgagcgcag aagtggtcct gcaactttat ccgcctccat   2760
ccagtctatt aattgttgcc gggaagctag agtaagtagt tcgccagtta atagtttgcg   2820
caacgttgtt gccattgcta caggcatcgt ggtgtcacgc tcgtcgtttg gtatggcttc   2880
attcagctcc ggttcccaac gatcaaggcg agttacatga tcccccatgt tgtgcaaaaa   2940
agcggttagc tccttcggtc ctccgatcgt tgtcagaagt aagttggccg cagtgttatc   3000
actcatggtt atggcagcac tgcataattc tcttactgtc atgccatccg taagatgctt   3060
```

```
ttctgtgact ggtgagtact caaccaagtc attctgagaa tagtgtatgc ggcgaccgag   3120
ttgctcttgc ccggcgtcaa tacgggataa taccgcgcca catagcagaa ctttaaaagt   3180
gctcatcatt ggaaaacgtt cttcggggcg aaaactctca aggatcttac cgctgttgag   3240
atccagttcg atgtaaccca ctcgtgcacc caactgatct tcagcatctt ttactttcac   3300
cagcgtttct gggtgagcaa aacaggaag gcaaaatgcc gcaaaaaagg gaataagggc    3360
gacacggaaa tgttgaatac tcatactctt ccttttcaa tattattgaa gcatttatca    3420
gggttattgt ctcatgagcg gatacatatt tgaatgtatt tagaaaaata aacaaatagg   3480
ggttccgcgc acatttcccc gaaaagtgcc acctgacgtc taagaaacca ttattatcat   3540
gacattaacc tataaaaata ggcgtatcac gaggccctt cgtctcgcgc gtttcggtga    3600
tgacggtgaa aacctctgac acatgcagct cccggagacg gtcacagctt gtctgtaagc   3660
ggatgccggg agcagacaag cccgtcaggg cgcgtcagcg ggtgttggcg ggtgtcgggg   3720
ctggcttaac tatgcggcat cagagcagat tgtactgaga gtgcaccata tgcggtgtga   3780
aataccgcac agatgcgtaa ggagaaaata ccgcatcagg cgccattcgc cattcaggct   3840
gcgcaactgt tgggaagggc gatcggtgcg ggcctcttcg ctattacgcc agctggcgaa   3900
agggggatgt gctgcaaggc gattaagttg ggtaacgcca gggttttccc agtcacgacg   3960
ttgtaaaacg acggccagtg aattcggcgc gccgagctcc tcgagcaaat ttacacattg   4020
ccactaaacg tctaaaccct tgtaatttgt ttttgtttta ctatgtgtgt tatgtatttg   4080
atttgcgata aattttttata tttggtacta aatttataac acctttatg ctaacgtttg    4140 ccaacactta gcaatttgca agttgattaa ttgattctaa attattttg tcttctaaat    4200 acatatacta atcaactgga aatgtaaata tttgctaata tttctactat aggagaatta   4260
aagtgagtga atatggtacc acaaggtttg gagatttaat tgttgcaatg ctgcatggat   4320
ggcatataca ccaaacattc aataattctt gaggataata atggtaccac acaagatttg   4380
aggtgcatga acgtcacgtg gacaaaaggt ttagtaattt ttcaagacaa caatgttacc   4440
acacacaagt tttgaggtgc atgcatggat gccctgtgga agtttaaaa atattttgga   4500 aatgatttgc atggaagcca tgtgtaaaac catgacatcc acttggagga tgcaataatg   4560
aagaaaacta caaatttaca tgcaactagt tatgcatgta gtctatataa tgaggatttt   4620
gcaatacttt cattcataca cactcactaa gttttacacg attataattt cttcatagcc   4680
agcccaccgc ggtgggcggc cgcctgcagt ctagaaggcc tcctgcttta atgagatatg   4740
cgagacgcct atgatcgcat gatatttgct ttcaattctg ttgtgcacgt tgtaaaaaac   4800
ctgagcatgt gtagctcaga tccttaccgc cggtttcggt tcattctaat gaatatatca   4860
cccgttacta tcgtattttt atgaataata ttctccgttc aatttactga ttgtccgtcg   4920
agcaaattta cacattgcca ctaaacgtct aaacccttgt aatttgtttt tgttttacta   4980
tgtgtgttat gtatttgatt tgcgataaat ttttatattt ggtactaaat ttataacacc   5040
ttttatgcta acgtttgcca acacttagca atttgcaagt tgattaattg attctaaatt   5100 attttgtct tctaaataca tatactaatc aactggaaat gtaaatattt gctaatattt    5160
ctactatagg agaattaaag tgagtgaata tggtaccaca aggtttggag atttaattgt   5220
tgcaatgctg catggatggc atatacacca aacattcaat aattcttgag gataataatg   5280
gtaccacaca agatttgagg tgcatgaacg tcacgtggac aaaaggttta gtaattttc    5340 aagcaacaa tgttaccaca cacaagtttt gaggtgcatg catggatgcc ctgtggaaag   5400
tttaaaaata                                                          5410
```

```
<210> SEQ ID NO 7
<211> LENGTH: 47
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(47)
<223> OTHER INFORMATION: USP1 forward

<400> SEQUENCE: 7
ccggaattcg gcgcgccgag ctcctcgagc aaatttacac attgcca         47

<210> SEQ ID NO 8
<211> LENGTH: 47
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(47)
<223> OTHER INFORMATION: USP2 forward

<400> SEQUENCE: 8
ccggaattcg gcgcgccgag ctcctcgagc aaatttacac attgcca         47

<210> SEQ ID NO 9
<211> LENGTH: 47
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(47)
<223> OTHER INFORMATION: USP3 forward

<400> SEQUENCE: 9
ccggaattcg gcgcgccgag ctcctcgagc aaatttacac attgcca         47

<210> SEQ ID NO 10
<211> LENGTH: 48
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(48)
<223> OTHER INFORMATION: USP1 reverse

<400> SEQUENCE: 10
aaaactgcag gcggccgccc accgcggtgg gctggctatg aagaaatt        48

<210> SEQ ID NO 11
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: USP2 reverse

<400> SEQUENCE: 11
cgcggatccg ctggctatga agaaatt                                27
```

<210> SEQ ID NO 12
<211> LENGTH: 45
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(45)
<223> OTHER INFORMATION: USP3 reverse

<400> SEQUENCE: 12
tcccccggga tcgatgccgg cagatctgct ggctatgaag aaatt         45

<210> SEQ ID NO 13
<211> LENGTH: 40
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(40)
<223> OTHER INFORMATION: OCS1 forward

<400> SEQUENCE: 13
aaaactgcag tctagaaggc ctcctgcttt aatgagatat         40

<210> SEQ ID NO 14
<211> LENGTH: 51
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(51)
<223> OTHER INFORMATION: OCS2 forward

<400> SEQUENCE: 14
cgcggatccg atatcgggcc cgctagcgtt aaccctgctt taatgagata t         51

<210> SEQ ID NO 15
<211> LENGTH: 33
<212> TYPE: DNA
<213> ORGANISM: unknown
<220> FEATURE:
<223> OTHER INFORMATION: artificial sequenc
<220> FEATURE:
<221> NAME/KEY: misc_feature
<222> LOCATION: (1)..(33)
<223> OTHER INFORMATION: OCS3 forward

<400> SEQUENCE: 15
tcccccgggc catggcctgc tttaatgaga tat         33

<210> SEQ ID NO 16
<211> LENGTH: 53
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(53)
<223> OTHER INFORMATION: OCS1 reverse

<400> SEQUENCE: 16
cccaagcttg gcgcgccgag ctcgaattcg tcgacggaca atcagtaaat tga         53

```
<210> SEQ ID NO 17
<211> LENGTH: 53
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(53)
<223> OTHER INFORMATION: OSC2 reverse

<400> SEQUENCE: 17
cccaagcttg gcgcgccgag ctcgaattcg tcgacggaca atcagtaaat tga        53

<210> SEQ ID NO 18
<211> LENGTH: 47
<212> TYPE: DNA
<213> ORGANISM: unknown
<220> FEATURE:
<223> OTHER INFORMATION: artificial sequence
<220> FEATURE:
<221> NAME/KEY: misc_feature
<223> OTHER INFORMATION: OSC3 reverse

<400> SEQUENCE: 18
cccaagcttg gcgcgccgag ctcgtcgacg gacaatcagt aaattga               47

<210> SEQ ID NO 19
<211> LENGTH: 28
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(28)
<223> OTHER INFORMATION: PcUBI4-2fw

<400> SEQUENCE: 19
gctctagaat tcgaatccaa aaattacg                                    28

<210> SEQ ID NO 20
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: PcUBI4-2rev

<400> SEQUENCE: 20
gggctgcaca tacataacat atcaaga                                     27

<210> SEQ ID NO 21
<211> LENGTH: 28
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(28)
<223> OTHER INFORMATION: Oligo1-GUS

<400> SEQUENCE: 21
ccatctcata aataacgtca tgcattac                                    28
```

```
<210> SEQ ID NO 22
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: probe GUS

<400> SEQUENCE: 22
tgtaaatcat cgcaagaccg gcaacag                                          27

<210> SEQ ID NO 23
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: Oligo2 GUS

<400> SEQUENCE: 23
aacatttggc aataaagttt cttaaga                                          27

<210> SEQ ID NO 24
<211> LENGTH: 20
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(20)
<223> OTHER INFORMATION: Oligo1 Ubi

<400> SEQUENCE: 24
agttcacccg aaaagcaacg                                                  20

<210> SEQ ID NO 25
<211> LENGTH: 33
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(33)
<223> OTHER INFORMATION: Probe Ubi

<400> SEQUENCE: 25
cccactgata atgatcgata tgtgaagaac tgc                                   33

<210> SEQ ID NO 26
<211> LENGTH: 20
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(20)
<223> OTHER INFORMATION: Oligo2 Ubi

<400> SEQUENCE: 26
tcgtcatgga accaccacct                                                  20
```

```
<210> SEQ ID NO 27
<211> LENGTH: 14
<212> TYPE: DNA
<213> ORGANISM: Artificial sequence
<220> FEATURE:
<223> OTHER INFORMATION: Consensus sequence of a heat shock-inducible
      element
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 27
ctngaanntt cnag                                                 14

<210> SEQ ID NO 28
<211> LENGTH: 15
<212> TYPE: DNA
<213> ORGANISM: Artificial sequence
<220> FEATURE:
<223> OTHER INFORMATION: Consensus sequence of a heat shock-inducible
      element
<220> FEATURE:
<221> NAME/KEY: misc_feature
<222> LOCATION: (8)..(8)
<223> OTHER INFORMATION: n is a, c, g, or t

<400> SEQUENCE: 28
ctggaatntt ctaga                                                15

<210> SEQ ID NO 29
<211> LENGTH: 4
<212> TYPE: PRT
<213> ORGANISM: Artificial sequence
<220> FEATURE:
<223> OTHER INFORMATION: Description of artificial sequence: plant
      transcription factor amino acid motif

<400> SEQUENCE: 29

Trp Arg Lys Tyr
1
```

METHOD FOR THE STABLE EXPRESSION OF NUCLEIC ACIDS IN TRANSGENIC PLANTS, CONTROLLED BY A PARSLEY-UBIQUITIN PROMOTER

RELATED APPLICATIONS

This application is a national stage application (under 35 U.S.C. 371) of PCT/EP2003/005668 filed on May 30, 2003, which claims benefit of German application 102 24 889.3 filed Jun. 4, 2002.

The Sequence Listing associated with this application is filed in electronic format via EFS-Web and hereby incorporated by reference into the specification in its entirety. The name of the text file containing the Sequence Listing is Revised_Sequence_List__13195__00004_US. The size of the text file is 36 KB, and the text file was created on Nov. 14, 2008.

FIELD OF THE INVENTION

The present invention relates to a process for stable expression of nucleic acids in transgenic plants.

The invention furthermore relates to nucleic acid constructs, vectors, transgenic plants and to the use of said transgenic plants for preparing foodstuffs, feedstuffs, seeds, pharmaceuticals or fine chemicals.

DESCRIPTION OF THE BACKGROUND

Various methods of introducing genes into the genome of plants are known (Halford N G, Shewry P R, Br Med Bull 2000; 56(1):62-73). The aim is the preparation of plants having advantageous, novel properties, for example to increase agricultural productivity, for improving the quality of foodstuffs or for producing particular chemicals or pharmaceuticals (Dunwell J M, J Exp Bot. 2000; 51 Spec No:487-96).

Moreover, the natural defence mechanisms of the plant, for example against pathogens, are inadequate. The introduction of foreign genes from plants, animals or microbial sources may enhance the defence, for example. Examples are the protection against insects feeding on tobacco by expression of the *Bacillus thuringiensis* endotoxin under the control of the 35 S CaMV promoter (Vaeck et al., Nature 1987, 328, 33-37) or the protection of tobacco against fungal infection by expression of a chitinase from beans under the control of the 35SCaMV promoter (Broglie et al., Science 1991, 254, 1194-1197).

It is furthermore possible to achieve resistance to herbicides by introducing foreign genes, thereby optimizing the cultivation conditions and reducing crop losses (Ott K H et al., J Mol Biol. 1996; 263(2):359-368).

The quality of the products may also be improved. Thus it is possible, for example, to increase the shelf life and storability of crop products by inactivating particular maturation genes. This has been demonstrated, for example, by inactivating polygalacturonase in tomatoes (Hamilton A J et al., Curr Top Microbiol Immunol 1995; 197: 77-89).

It is furthermore possible, by introducing further genes, advantageously metabolic genes, into plants, to enable particular products and by-products of naturally occurring metabolic processes to be utilized for a wide range of industries, including the feed, food, cosmetics and pharmaceutical industries. These molecules which are collectively referred to as "fine chemicals" include, for example, vitamins, amino acids, carbohydrates or lipids and fatty acids, one exemplary class of which are the polyunsaturated fatty acids (PUFAs). Polyunsaturated fatty acids are added, for example, to children's food in order to increase the nutritional value of these foods. PUFAs have, for example, a positive effect on the cholesterol level in the blood of humans and are therefore useful for protection against heart disease. Fatty acids and triglycerides have a multiplicity of applications in the food industry, animal nutrition, cosmetics and in the pharmaceutical sector.

A basic prerequisite for transgenic expression of particular genes in plants is the provision of plant-specific promoters. Various plant promoters are known. It is possible to distinguish between constitutive promoters which enable expression in various parts of a plant, which is only slightly restricted in terms of location and time, and specific promoters which allow expression only in particular parts or cells of a plant (e.g. root, seeds, pollen, leaves, etc.) or only at particular times during development. Constitutive promoters are advantageously used for expressing "selection markers". Selection markers (e.g. antibiotic or herbicidal resistance genes) permit filtering of the transformation event out of the multiplicity of untransformed but otherwise identical individual plants.

In all cases, it is necessary to control specifically expression of the genes to be expressed, depending on the function of said genes. Any expressed genes in any organisms have a promoter region 5' of the coding sequence. This region is responsible for the start of transcription itself and for regulating transcription. Said regulation is carried out usually by transcription factors binding to regulatory sequences within the promoter region. Promoters are usually freely portable within a species, i.e. it is possible to use a promoter of one gene in order to control transcription of another gene. This control of the new gene is then usually identical to controlling the original gene from which the promoter is derived. Thus it is possible to control expression of any gene in a known manner, using a known promoter whose regulation is known. This generally no longer applies, as soon as said promoter is used in other species. Thus, for example, promoters from the bacterium *Streptomyces* are recognized in the bacterium *E. coli* only poorly, if at all. The same applies to promoters of animal or plant origin which cannot readily be used reciprocally or in microorganisms.

Constitutive promoters active in plants have been described relatively rarely up to now. Promoters to be mentioned are the *Agrobacterium tumefaciens* TR double promoter, the promoters of the vacuolar ATPase subunits or the promoter of a proline-rich wheat protein (WO 91/13991) and also the Ppcl promoter *Mesembryanthemum crystallinum* (Cushman et al. (1993) Plant Mol Biol 21:561-566).

The constitutive promoters which are currently the predominantly used promoters in plants are almost exclusively of viral or bacterial origin, for example from *Agrobacterium*. In detail, these are the nopaline synthase (nos) promoter (Shaw et al. (1984) Nucleic Acids Res. 12(20):7831-7846), the mannopine synthase (mas) promoter (Comai et al. (1990) Plant Mol Biol 15 (3):373-381) and the octopine synthase (ocs) promoter (Leisner and Gelvin (1988) Proc Natl Acad Sci USA 85(5):2553-2557) from *Agrobacterium tumefaciens* and the CaMV35S promoter from cauliflower mosaic virus (U.S. Pat. No. 5,352,605). The latter is the most frequently used promoter in expression systems with ubiquitous and continuous expression (Odell et al.(1985) Nature 313:810-812; Battraw and Hall (1990) Plant Mol Biol 15:527-538; Benfey et al. (1990) EMBO J 9(69):1677-1684; U.S. Pat. No. 5,612,472). However, the CaMV 35S promoter which is frequently applied as constitutive promoter exhibits variations in its activity in different plants and in different tissues of the same plant (Atanassova et al. (1998) Plant Mol Biol 37:275-85; Battraw and Hall (1990) Plant Mol Biol 15:527-538; Holtorf et al. (1995) Plant Mol Biol 29:637-646; Jefferson et al. (1987) EMBO J 6:3901-3907). A further disadvantage of the 35S promoter is, for example, a change of it in transgene expression in the case of an infection with cauliflower mosaic virus and its typical pathogenic variants. Thus, plants expressing the BAR gene (Bialaphos resistance gene, alanylalanylphosphinothricine) under the control of the 35S promoter are no longer resistant after infection with the virus which typically occurs in nature (Al-Kaff et al. (2000) Nature Biotechnology 18:995-99).

From the range of viral promoters, the sugarcane bacilliform badnavirus (ScBV) which imparts an expression pattern similar to that of CamV has been described as an alternative to the CaMV 35S promoter (Schenk et al. (1999) Plant Mol Biol 39(6):1221-1230). The activity of the ScBV promoter was analyzed in transient expression analyses using various dicotyledonous plants, including *Nicotiana tabacum* and *N. benthamiana*, sunflower and oilseed rape, and monocotyledonous plants, here in the form of banana, corn and millet. In the transient analyses in corn, the ScBV promoter-mediated expression level was comparable to that of the ubiquitin promoter from corn (see below). Furthermore, the ScBV promoter-mediated rate of expression was assayed in transgenic banana and tobacco plants and displayed in both plant species essentially constitutive expression.

Common promoters for expressing selection markers in plants are especially the nos promoter, or else the mas promoter and ocs promoter, all of which have been isolated from *Agrobacterium* strains.

The use of viral sequences is often met with great reservations on the part of the consumer. These doubts are fed not least by studies which question the safety of the 35S CaMV promoter, owing to a possible horizontal gene transfer due to a recombination hot spot (Ho M W et al. (1999) Microbial Ecology in Health and Disease 11:194-197; Cummins J et al. (2000) Nature Biotechnology 18:363). It is therefore an aim of future biotechnological studies on plants to replace viral genetic elements by plant regulatory elements in order to keep as closely as possible to the plant system.

Owing to the prevailing doubts with regard to viral promoters, there are extensive efforts to replace said promoters by plant promoters. However, a promoter of plant origin, which is comparable to the viral elements, has not been described as yet.

What has been described, is a plant ubiquitin promoter from *Arabidopsis thaliana* (Callis et al. (1990) J Biol Chem 265:12486-12493; Holtorf S et al. (1995) Plant Mol Biol 29:637-747). However, some studies revealed that the *Arabidopsis* ubiquitin promoter is unsuitable for expressing selection marker genes.

Christensen et al. have described further promoters, namely the two corn ubiquitin promoters Ubi-1 and Ubi-2, which exhibit heat inducibility, in addition to constitutive basic expression (U.S. Pat. Nos. 5,510,474; 6,020,190 and 6,054,574). The expression pattern of the two promoters Ubi-1 and Ubi-2 from corn is described in Plant. Mol. Biol., (1992), 18(4):675-689. While the Ubi-1 promoter has good expression activity in corn and other monocotyledonous plants, it exhibits in dicotyledonous tobacco plants only 10% of the activity which had been achieved in comparable experiments using the viral 35S promoter. The corn Ubi-1 promoter is thus suitable for overexpression of genes in monocotyledonous plant systems. In addition, it is sufficiently strong in order to mediate a herbicidal resistance via expression of selection markers [Christensen and Quail (1996) Transgenic Res 5(3):213-218]. However, the Ubi-1 promoter proved unsuitable for dicotyledonous expression systems.

WO01/18220 describes a ubiquitin regulatory system which lacks the heatshock elements, i.e. it is no longer heat-inducible. This regulatory system was developed, starting from the corn Ubi-promoter system, by removing the heat-inducible elements.

Ubiquitins are omnipresent proteins which have been found in all eukaryotes analyzed thus far. Thus, Kawalleck et al. [Plant Molecular Biology, 21, 1993: 673-684] describe two parsley (*Petroselinum crispum*) ubiquitins, ubi4-1 and ubi4-2. The promoter of ubi4-2 has been isolated. It was not possible to demonstrate any heat inducibility of ubi4-1 and ubi4-2 under the conditions studied by Kawalleck et al.

A comparison of the organ specificity and strength of various constitutive promoters was carried out by Holtorf (Holtorf et al. (1995) Plant Mol Biol 29(4):637-646) on the basis of stably transformed *Arabidopsis* plants. The study comprised, inter alia, the CaMV35S promoter, the leaf-specific thionine promoter from barley and the *Arabidopsis* ubiquitin promoter (UBQ1). The CaMV35S promoter exhibited the highest rate of expression. On the basis of using an additional translational enhancer (TMV omega element), it was possible to increase the rate of expression of the promoter by a factor of two to three with unchanged organ specificity. The leaf-specific thionine promoter from barley was inactive in the majority of transformed lines, while the UBQ1 promoter from *Arabidopsis* resulted in medium rates of expression.

McElroy and colleagues reported a construct for transforming monocotyledonous plants, which is based on the rice actin 1 (Act1) promoter (McElroy et al. (1991) Mol Gen Genet 231:150-1609). Overall, it was concluded from the afore-described studies that the Act1promoter-based expression vectors are suitable for controlling a sufficiently strong and constitutive expression of foreign DNA in transformed cells of monocotyledonous plants.

Another constitutive promoter which has been described is the promoter of an S-adenosyl-L-methionine synthetase (WO 00/37662). A disadvantage here is especially a dependence of the strength of expression on the methionine concentration.

WO 99/31258 describes chimeric constitutive plant promoters which are composed of various elements of various promoters with complementary expression patterns so that the combination of individual tissue specificities additively results in a constitutive expression pattern. This is a very complicated process for preparing apparently constitutive promoters.

Furthermore, promoters have been described which have specificities for the anthers, ovaries, flowers, leaves, stalks, roots and seeds. The stringency of the specificity and also the expression activity of said promoters is very different. Promoters which may be mentioned are those which ensure leaf-specific expression, such as the potato cytosolic FBPase promoter (WO 97/05900), the rubisco (ribulose-1,5-bisphosphate-carboxylase) SSU (small subunit) promoter, the potato ST-LSI promoter [Stockhaus et al. (1989) EMBO J 8:2445-2245], the mainly leaf-specific ferredoxin NADPH oxidoreductase promoter (FNR promoter) which has a light-inducible element [Oelmüller et al. (1993) Mol. Gen. Genet. 237:261-72] or the leaf-specific promoter of the triose-phosphate translocator (TPT).

Examples of further promoters are promoters with specificity for tubers, storage roots or roots, such as, for example, the patatin class I promoter (B33), the potato cathepsin D inhibitor promoter, the starch synthase (GBSS1) promoter or the sporamin promoter, fruit-specific promoters such as, for example, the tomato fruit-specific promoter (EP-A 409625), fruit maturation-specific promoters such as, for example, the tomato fruit maturation-specific promoter (WO 94/21794), flower-specific promoters such as, for example, the phytoene synthase promoter (WO 92/16635) or the promoter of the P-rr gene (WO 98/22593).

A promoter regulated as a function of development is described, inter alia, in Baerson et al. (Baerson S R, Lamppa G K (1993) Plant Mol Biol 22(2):255-67).

Promoters have been described which have tissue specificity for the mesophyll and the pallisade cells in leaves (Broglie et al. (1984) Science 234:838-845), the dividing shoot and the root meristem [Atanassova et al. (1992) Plant J 2:291-300], pollen [Guerrero et al. (1990) Mol Gen Genet 224:161-168], seed endosperm [Stalberg et al. (1993) Plant Mol Biol 23:671-6839, root epidermis [Suzuki et al. (1993) Plant Mol Biol 21:109-119], and for the root meristem, root vascular tissue and root knots [Bogusz et al. (1990) Plant Cell 2:633-641].

Other known promoters are those which control expression in seeds and plant embryos. Examples of seed-specific promoters are the phaseolin promoter [U.S. Pat. No. 5,504,200, Bustos M M et al. (1989) Plant Cell 1(9):839-53], the promoter of the 2S albumin gene [Joseffson L G et al. (1987) J Biol Chem 262:12196-12201], the legumin promoter [Shirsat A et al. (1989) Mol Gen Genet 215(2):326-331], the promoters of the USP [unknown seed protein; Bäumlein H et al. (1991) Molecular & General Genetics 225(3):459-67], of the napin gene [Stalberg K, et al. (1996) Planta 199:515-519], of the saccharose-binding protein (WO 00/26388) and the LeB4 promoter [Bäumlein H et al.(1991) Mol Gen Genet 225:121-128]. Said promoters control seed-specific expression of storage proteins.

Many of the abovementioned promoters exhibit, in addition to the primary activity, also "secondary activities" in other tissues.

Owing to the tissue-dependent expression pattern, the abovementioned tissue-specific promoters are poorly suited to expressing selection markers. Here, a selection in all tissue parts, if possible, is required in order to ensure efficient selection.

The "constitutive" promoters described in the prior art have one or more of the following disadvantages:

1. Inadequate homogeneity of expression:
   The known "constitutive" promoters frequently display a different level of expression, depending on the type of tissue or cell. Moreover, the expression property is often highly dependent on the site of insertion into the host genome. This indicates that the effects to be obtained by heterologous expression cannot be achieved to the same extent homogeneously in the plant. Under or over dosages may occur. This may have an adverse effect on plant growth or plant value.

2. Inadequate time profile:
   The "constitutive" promoters known in the prior art often exhibit a nonconsistent activity during the development of a tissue. As a result, it is not possible, for example, to achieve desirable effects (such as selection) in the early phase of somatic embryogenesis which would be advantageous, especially here, due to the sensitivity of the embryo to in vitro conditions and stress factors.

3. Inadequate applicability to many plant species:
   The "constitutive" promoters described in the prior art are often not active in the same way in all species.

4. Gene silencing
   If a plurality of expression cassettes with in each case the same "constitutive" promoter are present in an organism, interactions between said expression cassettes and even switching-off (gene silencing) of individual expression cassettes may occur (Mette et al. (1999) EMBO J. 18:241-248).

5. Viral and bacterial promoters
   Promoters of viral origin may be influenced by virus infections of the transgenic plant and may then no longer express the desired property (Al-Kaff et al. (2000) Natur Biotechnology 18:995-99).
   The public acceptance toward the use of promoters and elements from plant systems is higher than for viral systems.
   The number of promoters suitable for expressing selection markers in plants is low and said promoters are usually of viral or bacterial origin.

An ideal constitutive promoter should have as many of the following properties as possible:

a) A gene expression which is as homogeneous as possible with regard to location and time, i.e. an expression in as many cell types or tissues of an organism as possible during the various phases of the developmental cycle. Desirable expression should take place as early as in the embroyo stage. Furthermore, an efficient selection in dedifferentiated cells (various callus phases) from a tissue culture and other developmental stages suitable for tissue culture is desired.

b) An applicability to various plant species, which is as broad as possible, and applicability to species in which it is not possible to achieve any expression using the "constitutive" promoters known to date.

c) In order to combine a plurality of transgenes in one plant, it is desirable to carry out a plurality of transformations in succession or to use constructs with a plurality of promoter cassettes, but without generating silencing effects due to the multiple use of identical regulatory sequences.

d) A plant origin in order to avoid problems of acceptance by the consumer and possible problems of future approval.

SUMMARY OF THE INVENTION

The present invention provides, generally, processes for the stable expression of nucleic acids in plants. The invention further provides materials such as nucleic acid constructs, vectors and transgenic plants useful in these and conventional processes, and foodstuffs, feedstuffs, seeds, pharmaceuticals and fine chemicals made with these materials and processes.

One embodiment of the invention is directed to processes for expressing nucleic acids in transgenic plants under the control of a parsley ubiquitin promoter, wherein the process comprises: linking a nucleic acid to be expressed to a promoter containing the sequence of SEQ ID NO: 1 or to a functional equivalent or equivalent fragment which has essentially the same promoter activity as said promoter, to form a construct; and introducing into a plant the construct under conditions which enable the nucleic acid to be stably integrated into the genome of said plant.

Another embodiment of the invention is directed to nucleic acid constructs for stable transgenic expression of nucleic acids comprising: a promoter containing the sequence of SEQ ID NO: 1, or one or more functional equivalents or equivalent fragments of said promoter, which have essentially the same promoter activities as said promoter, wherein said promoter is functionally linked to a nucleic acid sequence to be expressed transgenically.

Another embodiment of the invention is directed to vectors comprising the nucleic acid constructs of the invention.

Another embodiment of the invention is directed to transgenic plants transformed with the nucleic acid constructs of the invention.

Another embodiment of the invention is directed to methods for preparing foodstuffs, feedstuffs, seeds, cosmetics, pharmaceuticals or fine chemicals comprising the transgenic plants of the invention.

BRIEF DESCRIPTION OF THE DRAWINGS

FIG. 1 shows the expression vector construct 1bxPcUbi4-2GUS.

FIG. 2 shows GUS staining of leaves of independent transgenic C24 *Arabidopsis* plants containing the GUS gene under the control of the PcUbi4-2 *P. crispum* promoter.

FIG. 3 shows GUS staining of leaves of independent transgenic C24 *Arabidopsis* plants containing the GUS gene under the control of the d35S promoter.

FIG. 4 shows GUS staining of the bud of a transgenic C24 *Arabidopsis* plant containing the GUS gene under the control of the Pc-Ubi4-2 *P. crispum* promoter.

FIG. 5 shows GUS staining of the flower of a transgenic C24 *Arabidopsis* plant containing the GUS gene under the control of the Pc-Ubi4-2 *P. crispum* promoter.

FIG. 6 shows GUS staining of the root of a transgenic C24 *Arabidopsis* plant containing the GUS gene under the control of the Pc-Ubi4-2 *P. crispum* promoter.

FIG. 7 shows GUS staining of seeds of transgenic C24 *Arabidopsis* plants containing the GUS gene under the control of the *P. crispum* Pc-Ubi4-2 promoter (middle and right) or under the control of the d35S promoters (left).

FIG. 8 shows the sequence of pcUbi4-2 (SEQ ID NO: 1).

The object on which the present invention is based was therefore to provide a process for stable expression of nucleic acids in transgenic plants under the control of a plant promoter which fulfils as many of the abovementioned properties as possible and which mediates especially a ubiquitous and development-independent (constitutive) expression of a nucleic acid sequence to be expressed—which preferably encodes a selection marker. It was furthermore the object to provide a nucleic acid construct for the expression process, which enables the expressed nucleic acid to be expressed as broadly as possible in various plant tissues and which is broadly applicable in various plants.

This object was achieved by a process for expressing nucleic acids in transgenic plants under the control of a parsley ubiquitin promoter, wherein the process comprises the following steps:
a) linking the nucleic acid to be expressed to a promoter according to SEQ ID NO: 1 or to
b) a functional equivalent or equivalent fragment which essentially has the same promoter activity as a), and
b) introducing into a plant the nucleic acid construct composed of said nucleic acid to be expressed which is under the control of the 5' region of the promoter mentioned under a) or b) and said promoter, under conditions which enable the nucleic acid to be stably integrated into the plant genome.

The nucleic acid to be expressed in the process of the invention may advantageously be functionally linked to further regulatory sequences.

Expression comprises, for the purpose of the process, transcription of the nucleic acid sequence to be expressed transgenically, but may also comprise, in the case of an open reading frame in "sense" orientation, translation of the transcribed RNA of said nucleic acid sequence to be expressed transgenically into a corresponding polypeptide.

A promoter activity is referred to as being essentially the same when transcription/translation, for example of the GUS gene described below [=β-glucuronidase gene, uida, Jefferson, R. A., Kavanagh, T. A., Bevan, M. V. (1987) GUS fusions: β-Glucuronidase as a sensitive and versatile gene fusion marker in higher plants. EMBO J. 6, 3901-3907; Martin, T., Wöhner, R. V., Hummel, S., Willmitzer, L., Frommer, W. B. (1992) The GUS reporter system as a tool to study plant gene expression. In: Gallagher (editor): GUS Protocols: Using the GUS gene as a reporter of gene expresion. Academic Press, 23-43] differs by no more than 50%, advantageously by no more than 40%, preferably by no more than 30%, particularly preferably by no more than 20%, very particularly preferably by no more than 10%, from a comparative value determined using that under SEQ ID NO: 1. The level of expression may deviate here both downward and upward, in comparison with a comparative value.

Preference is given here to those sequences whose level of expression, measured on the basis of the transcribed mRNA, differs from a comparative value obtained using the promoter described by SEQ ID NO: 1 quantitatively by no more than 50, preferably 25%, particularly preferably 10%, under otherwise unchanged conditions. Preference is further given to the comparative value being the level of expression obtained with any, but specific, nucleic acid sequence, preferably those nucleic acid sequences coding for readily quantifiable proteins. Advantageously, use is made here of reporter proteins (Schenborn E, Groskreutz D. Mol Biotechnol. 1999; 13(1): 29-44) such as green fluorescence protein (GFP) (Chui W L et al., Curr Biol 1996, 6:325-330; Leffel S M et al., Biotechniques. 23(5):912-8, 1997), chloramphenicol transferase or a luciferase (Millar et al., Plant Mol Biol Rep 1992 10:324-414) or β-galactosidase, with β-glucuronidase being very particularly preferred (Jefferson et al., EMBO J. 1987, 6, 3901-3907).

The aforementioned parsley ubiquitin promoter used in the process of the invention exhibited in the nucleic acid construct an advantageous strong expression of the expressed nucleic acids in virtually all plant tissues, including that of seeds. Advantageously, the process of the invention results in stable strong expression of the nucleic acids in a very large number of individuals, i.e. the nucleic acid or nucleic acids expressed in the process of the invention (for the application, the singular is intended to comprise the plural and vice versa) is/are expressed very evenly in the transgenic plants, independently of their site of insertion and independently of the tissue. "Gene silencing" in which the expression activity of the nucleic acids or genes to be expressed is down-regulated or even switched off completely due to interactions in the genome of the host organism, in the case of the present process in the transgenic plant, occurs only negligibly, if at all. The process of the invention thus achieves strong expression of the nucleic acids in at least 60%, advantageously at least 70%, preferably at least 80%, particularly preferably at least 90%, very particularly preferably at least 95%, of the transgenic plants generated in said process. The process or the nucleic acid construct of the invention is thus insensitive to epigenetic influences. FIG. 2 depicts this advantageous property of the process of the invention for GUS staining of leaves of transgenic C24 *Arabidopsis* plants which again the GUS gene (=β-glucoronidase gene, uida) under the control of the PcUbi4-2 promoter from *P. crispum*. 48 independent T1 lines were studied. FIG. 1 illustrates the construction of an advantageously used vector. A comparison with the prior art, in which the GUS gene was inserted downstream of the d35S promoter, can be found in FIG. 3. The advantageous properties of the process are clearly revealed. FIG. 3 represents GUS staining of leaves of transgenic C24 *Arabidopsis* plants containing the GUS gene under the control of the d35S promoter. Likewise, 48 independent T1 lines were studied. Moreover, the d35S promoter exhibited also a different expression strength within one leaf of a plant, i.e. it exhibited a mosaic-like expression dependent on the different situation within one leaf of a plant. In contrast, the expression behavior under the control of the PcUbi4-2 promoter within one leaf of a plant is very homogeneous, i.e. no mosaic-like expression is visible. The process thus enables genes to be expressed strongly and evenly in stably transformed plants.

Evenly strong expression means for the purpose of the invention that the nucleic acid is expressed within a plant tissue in at least 60%, advantageously at least 70%, preferably at least 80%, particularly preferably at least 90%, very particularly preferably at least 95%, of the cells of a tissue.

Besides strong expression in the leaf, the process of the invention also achieves strong expression of the nucleic acids used in said process in other tissues. Thus, strong expression is likewise achieved in the bud, the flower, the root, the stem and the seeds. FIG. 4 indicates expression of a transgenic C24 *Arabidopsis* plant containing the GUS gene under the control of the Pc-Ubi4-2 promoter from *P. crispum* in the bud. The dark gray regions indicate β-glucoronidase expression. FIG. 5 represents GUS staining of the flower of a transgenic C24 *Arabidopsis* plant containing the GUS gene under the control of the Pc-Ubi4-2 promoter from *P. crispum*. The dark gray regions can be attributed to the enzymic activity of the expressed β-glucoronidase. In the root of transgenic C24 *Arabidopsis* plants containing the GUS gene under the control of the Pc-Ubi4-2 promoters from *P. crispum*, strong expression can also be observed, as FIG. 6 reveals. Here too, the dark gray regions represent the β-glucoronidase activity. The same also applies to expression in seeds, as FIG. 7 reveals. FIG. 7 shows the GUS staining of seeds of transgenic C24 *Arabidopsis* plants which contain the GUS gene under the control of the Pc-Ubi4-2 promoter from *P. crispum* (middle and right) or under the control of the d35S promoter (left). The dark gray supernatant reflects the β-glucoronidase activity. The Pc-Ubi4-2 promoter can clearly be seen as having a higher activity in the seeds than the d35S promoter.

Using the process of the invention, strong expression of the nucleic acids used is thus achieved in almost all transgenic plants. Moreover, this strong expression advantageously takes place in all plant tissues studied. The process and the nucleic acid constructs of the invention are therefore advantageously suitable for expressing a virtually unlimited number of genes in plants such as monocotyledonous or dicotyledonous plants, advantageously dicotyledonous plants. Selection genes may advantageously be expressed under the control of the advantageous promoter in the process. Advantageously, expression is carried out constitutively, but an induction, for example via a heat action, is conceivable. FIG. 8 indicates the elements important to the function of the promoter, such as a possible putative heat shock-inducible element (=HSE, position 534-547). This may increase expression further. The HSE is located within the intron region. This heat shock-inducible element does not correspond to the consensus sequences 5'-CTNGAANNTTC-NAG-3' (SEQ ID NO: 27) and, respectively, CTGGAATNT-TCTAGA-3' (SEQ ID NO: 28, U.S. Pat. No. 5,510,474) indicated by Mycogen or to that of drosophila (U.S. Pat. No. 6,054,574, column 18, row 59-64) and has not been recognized as an HSE in a promoter analysis of plant cis-active elements, using the internet page PLACE. Moreover, in contrast to the HSE annotated in the Mycogen patents, the intron is in the intron and not, as described by Mycogen, 5' relative to and thus upstream of the intron.

Moreover, FIG. 8 shows the following further elements which have been found using that of Higo et al. [(1999) Plant cis-acting regulatory DNA elements (PLACE) database: 1999, Nucl. Acid. Res., Vol. 27, No. 1, 297-300]:

a) two CAAACAC elements, position 264 to 270 and 716 (counterstrand), conserved in many storage protein promoters, necessary for expressing the napA promoter in seeds [Stalberg K, Ellerstom M, Ezcurra I, Ablov S, Rask L Disruption of an overlapping E-box/ABRE motif abolished high transcription of the napA storage-protein promoter in transgenic *Brassica napus* seeds. Planta 199:515-519 (1996)]

b) two AACAAAC elements, position 140 to 146 and 461 (counterstrand), important for endosperm-specific expression [Wu C, Washida H, Onodera Y, Harada K, Takaiwa F Quantitative nature of the Prolamin-box, ACGT and AACA motifs in a rice glutelin gene promoter: minimal cis-element requirements for endosperm-specific gene expression Plant J 23: 415-421 (2000)]

c) one TATA box (TATATATA) in the region from 291 to 297 and thus at the expected distance to the transcription start at position 237. [Joshi C P. An inspection of the domain between putative TATA box and translation start site in 79 plant genes. Nucleic Acids Research. 15(16):6643-53, 1987 Aug. 25.]

The elements mentioned under a) to c) are marked by boxes in FIG. 8, with the AACAAAC and CAAACAC boxes of the counterstrand being especially emphasized. The transcription start is indicated by an arrow. Moreover, the promoter contains an intron, immediately upstream of the translation start (position 396 to 982, see FIG. 8). The intron is followed immediately by the start codon ATG (not indicated).

The program moreover identified the following further putative elements of the promoter:

A total of four ACGTA boxes (positions 214, 674, 692, 880) important, inter alia, also for sugar repression and expression in seeds. Abscisic acid-responsive element (227) [Hattori T, Totsuka M, Hobo T, Kagaya Y, Yamamoto-Toyoda A Experimentally Determined Sequence Requirement of ACGT-Containing Abscisic Acid Response Element Plant Cell Physiol 43: 136-140 (2002)]; several "amylase boxes", positions 139, 421 (counterstrand), 462 (counterstrand), 789 (counterstrand) and 871 (counterstrand) [Huang N, Sutliff T D, Litts J C, Rodriguez R L Classification and characterization of the rice alpha-amylase multigene family. Plant Mol Biol 14:655-668 (1990)]; a CACGTG motif in position 565, present, inter alia, in light-regulated promoters [Menkens A E, Schindler U, Cashmore A R The G-box: a ubiquitous regulatory DNA element in plants bound by the GBF family of bzip proteins Trends in Biochemistry 20:506-510 (1995)]; a total of 16 GATA boxes, involved in strong light-dependent expression [Gilmartin P M, Sarokin L, Memelink J, Chua N-H Molecular light switches for plant genes. Plant Cell 2:369-378 (1990)]; 5 GT1 consensus binding sites (GR-WAAW) which are present in many light-regulated genes can be found in position 395 and also on the counterstrand, positions 52, 387, 504 and 647 [Villain P, Mache R, Zhou D X The mechanism of GT element-mediated cell type-specific transcriptional control. J Biol Chem 271:32593-32598 (1996)]; an Ibox (GATAAG) can be found in position 474 on the counterstrand. This is a conserved element in light-regulating promoters [Rose A, Meier I, Wienand U The tomato I-box binding factor LeMYBI is a member of a novel RT class of Myb-like proteins Plant J 20: 641-652 (1999)]; an LTRE (low-temperature-responsive element), CCGAAA, can be found in position 632 [Dunn M A, White A J, Vural S, Hughes M A Identification of promoter elements in a low-temperature-responsive gene (blt4.9) from barley (Hordeum RT vulgare L.) Plant Mol Biol 38:551-564 (1998)]; several binding sites for various classes of myb transcription factors [Jin H. Martin C. Multifunctionality and diversity within the plant MYB-gene family. Plant Molecular Biology. 41(5):577-85, 1999 November]; several W-box binding sites (549, 61, 550, 919) which are bound by WRKY (SEQ ID NO: 29) transcription factors. The factors are involved in different physiological processes such as pathogen defence, senescence and trichome formation [Eulgem T, Rushton P J, Robatzek S, Somssich I E R T The WRKY superfamily of plant transcription factors RL Trends Plant Sci (2000) 5:199-206] (SEQ ID NO: 29).

The TATA box indicated (see FIG. 8) is essential for the function of the promoter. It should advantageously be located in a region from −20 to −50, preferably from −25 to −35, from the transcription start.

A sequence comparison between PcUbi4-2 and the corn Ubi promoter demonstrates that the genes of corn and *P. crispum* are 66.1% identical at the nucleotide level, while the promoters are 26% identical, i.e. there is no significant identity for AT-rich promoters (Gap opening penalty 15, Gap extension penalty 6.66) [Altschul et al., 1990, J. Mol. Biol., 215:403-410, Altschul et al., 1997, Nucl. Acid Res., 25:3389-3402]. In Blast, the promoters cannot find each other.

The ubiquitin promoter advantageously used in the process of the invention proved to be sufficiently strong in order to express nucleic acid sequences, in particular selection marker genes in dicotyledones and monocotyledones, which had successfully been stably integrated into the genome of the plant. This is all the more surprising, since the *Arabidopsis thaliana* ubiquitin promoter [Holtorf et al. (1995) Plant Mol Biol 29:637-646] proved not suitable.

Said advantageously used ubiquitin promoter may be optimized further for its task by methods known to the skilled worker. The skilled worker may readily isolate improved mutants of the promoter via the assay given in the examples, with the aid of β-glucuronidase.

In this context, mutations comprise substitutions, additions, deletions, inversions or insertions of one or more nucleotide residues. Thus, for example, the present invention also comprises those nucleotide sequences which are obtained by modification of the ubiquitin promoter according to SEQ ID NO: 1. The aim of such a modification may be further narrowing of the essential promoter sequence present therein or, for example, also the introduction of further restriction enzyme cleavage sites, the removal of excess DNA or the addition of further sequences, for example further regulatory sequences.

Where insertions, deletions or substitutions such as, for example, transitions and transversions are suitable, techniques known per se, such as in vitro mutagenesis, primer repair restriction or ligation may be used. Manipulations such as, for example, restriction, chewing back or filling in protruding ends to give blunt ends may provide complementary ends of the fragments for ligation. Analogous results may also be obtained using the polymerase chain reaction (PCR) using specific oligonucleotide primers.

Functional equivalents or functional fragments derived from SEQ ID NO: 1, for example by substitution, insertion or deletion of nucleotides, are at least 30%, preferably 50%, preferentially at least 70%, particularly preferably at least 90%, very particularly preferably at least 95%, homologous and are characterized by essentially the same properties as the parsley ubiquitin promoter according to SEQ ID NO: 1.

These functional equivalents can be generated artificially or else isolated from various organisms such as plants by means of homology comparisons and biochemical assays.

Alternatively, nonessential sequences of the parsley promoter may be deleted, without substantially impairing the promoter property. Such deletion variants are functionally equivalent parts of the promoter, described by SEQ ID NO: 1.

Advantageously, the process of the invention uses for stable expression of nucleic acids in transgenic plants, which encode a gene selected from the group consisting of a selection marker, a reporter gene, an RNAi construct, an enzyme, a protein which mediates resistance to insects, viruses, bacteria, fungi or nematodes, a nucleic acid sequence or a protein which mediates in plants resistance to drought, cold, heat or salt, an inhibitor, a lectin, an RNAase, a ribozyme, an antibody, a vaccine, a pharmaceutical, an anti-freezing protein, a cytochrome P-450 protein, a transcription activator or repressor or a protein involved in the biosynthesis of fine chemicals.

Preference is given to the protein involved in the biosynthesis of fine chemicals being a protein of the fatty acid metabolism, the amino acid metabolism, the vitamin metabolism, the carotenoid metabolism or the carbohydrate metabolism.

If, in addition to the aforementioned genes, further genes or nucleic acids are intended to be expressed in the process of the invention, then the latter may likewise be expressed under the control of the parsley ubiquitin promoter or else advantageously under the control of other promoters which may be constitutive, inducible and/or tissue-specific.

The nucleic acid to be expressed in the process may be oriented to the promoter and thus expressed in the sense or antisense direction or in the sense and antisense direction (=dsRNAi).

Advantageously, the nucleic acid construct used in the process is inserted between two T-DNA sections. This facilitates stable ingegration into the plant genome.

The transgenic plant used in the process is a monocotyledonous or dicotyledonous plant, advantageously a dicotyledonous plant.

Examples of monocotyledonous plants which may be mentioned are monocotyledones selected from the group consisting of corn, rice, triticale, wheat, rye, barley, oats, rye grass or millet.

Examples of dicotyledonous plants which may be mentioned are dicotyledones selected from the group consisting of oilseed rape, evening primrose, canola, peanut, verbascum, thistle, hazelnut, almond, macadamia, avocado, bay, wild roses, pumpkin, pistachios, sesame, linseed, sunflower, safflower, soybean, borage, poppy, mustard, hemp, castor-oil plant, olive, calendula, punica, sugar beet, tomato, potato, tobacco, carrot, poplar, cotton, manioc, pepper, *tagetes,* eggplant, pea, alfalfa, coffee, cocoa, tea, oil palm, coconut, walnut or *Arabidopsis.*

As mentioned above, the nucleic acids used in the process of the invention may be expressed constitutively or inducibly. Preference is given to constitutive expression.

If, for example, fine chemicals are prepared in the process, the products produced in the transgenic plants due to expression of the nucleic acids may be isolated from said plants after culturing of the latter. In this context, the products may be isolated from callus cultures, from fermentation cultures or from cultured and harvested plants or plant parts such as leaves, stalk, root, flower or seeds, by methods known to the skilled worker.

An example of a fine chemical which may be prepared and isolated according to the process of the invention, which may be mentioned by way of example, are fatty acid esters having polyunsaturated $C_{18}$, $C_{20}$ and/or $C_{22}$ fatty acid molecules. These may be isolated in the form of an oil or lipid, for example in the form of compounds such as sphingolipids, phosphoglycerides, lipids, glycolipids such as glycoshingolipid, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids having at least two, preferably three, double bonds. As a rule, the different abovementioned compounds (fatty acid esters and free fatty acids) are present in the plant in an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the different compounds making 100% by weight.

Advantageously, it is possible to prepare and isolate in the process of the invention linoleic acid (C18:2), linolenic acid (C18:3), arachidonic acid (ARA) or eicosapentaenoic acid (EPA).

It is advantageous to use, in the process of the invention, plants which belong to the oil-producing plants, i.e. which are used for the production of oils, such as oil crops, which comprise large amounts of lipid compounds, such as peanut, oilseed rape, canola, sunflower, safflower, poppy, mustard, hemp, castor-oil plant, olive, sesame, calendula, punica, evening primrose, verbascum, thistle, wild roses, hazelnut, almond, macadamia, avocado, bay, pumpkin, linseed, soybean, pistachios, borage, trees (oil palm, coconut or walnut) or field crops such as maize, wheat, rye, oats, triticale, rice, barley, cotton, manioc, pepper, *tagetes,* Solanaceae plants such as potato, tobacco, eggplant and tomato, *Vicia* species, pea, alfalfa or bush plants (coffee, cacao, tea), *Salix* species and perennial grasses and fodder crops. Preferred plants are oil crops such as peanut, oilseed rape, canola, sunflower, safflower, poppy, mustard, hemp, castor-oil plants, olive, calendula, punica, evening primrose, pumpkin, linseed, soybean, borage, trees (oil palm, coconut). Especially preferred are plants which are high in C18:2- and/or C18:3-fatty acid, such as sunflower, safflower, tobacco, verbascum, sesame, cotton, pumpkin, poppy, evening primrose, walnut, linseed, hemp, thistle or safflower. Very especially preferred are plants such as safflower, sunflower, poppy, evening primrose, walnut, linseed or hemp.

When preparing PUFAS in the process of the invention, nucleic acids are expressed which encode, for example, polypeptides having $\Delta 5$-, $\Delta 6$-desaturase or $\Delta 6$-elongase activity. Depending on the selection of the plant used for the process of the invention, mixtures of the various aforementioned compounds or individual compounds such as EPA or ARA can be prepared in free or bound form.

In the process of the invention, transgenic plants also mean plant cells, plant tissue, plant organs or intact plants which are suitable for expression of nucleic acids. Growing is understood as meaning for example culturing of the transgenic plant cells, plant tissue or plant organs on a nutrient medium or the intact plant on or in a substrate, for example in hydroponic culture or on an arable soil.

In principle, it is possible to use any nucleic acids in the process of the invention. Advantageously, said nucleic acids are derived from plants such as algae, diatoms, mosses or higher plants, or else may be derived from microorganisms such as fungi, yeasts, or from animals such as nematodes, insects or humans.

The transgenic plant means, for the purposes of the invention, that the nucleic acids used in the process are not stably integrated at their natural locus in the genome of a plant; in this context, the nucleic acids can be expressed homologously or heterologously. However, transgenic also means that, while the nucleic acids according to the invention are at their natural locus in the genome of an organism, the sequence has been modified in comparison with the natural sequence and/or the regulatory sequences of the natural sequences have been modified. Preferably, transgenic is understood as meaning that the nucleic acids according to the invention are not expressed at their natural locus in the genome, that is to say that homologous or preferably heterologous expression of the nucleic acids takes place.

Transgenic plants which comprise the nucleic acids expressed in the process of the invention can be marketed directly without isolation of the compounds which have been synthesized. Plants mean, in the process of the invention, all plant parts, plant organs such as leaf, stem, root, tuber or seeds, or all of the plant. In this context, the seed comprises all parts of the seed such as the seed coats, epidermis cells and seed cells, endosperm or embryo tissue. However, the compounds produced in the process of the invention can also be isolated from the plants in the form of the free products, for example their oils, fat, lipids and/or free fatty acids. Compounds which have been produced by this process can be harvested by harvesting the organisms either from the culture in which they grow or from the field. This can be done, for example in the case of oils, by pressing or extracting the plant parts, preferably the plant seeds, in a manner known to the skilled worker. In this context, the oils, fats, lipids and/or free fatty acids can be obtained by pressing by what is known as cold-beating or cold-pressing, without supplying heat. The plant parts, specifically the seeds, are beforehand comminuted, steam-treated or toasted in order to facilitate their disruption. The seeds pretreated thus can subsequently be pressed or else extracted with solvents such as warm hexane. The solvent is subsequently removed. In this manner, more than 96% of the compounds produced in the process can be isolated. The resulting products are subsequently processed further, i.e. refined. Here, the plant mucilages and turbid matter are first. What is known as degumming can be performed enzymatically or, for example, chemico-physically by adding acid such as phosphoric acid. The free fatty acids are subsequently removed by treatment with a base, for example sodium hydroxide solution. The resulting product is washed thoroughly with water to remove the alkali remaining in the product, and dried. To remove the coloring matter which still remains in the product, the products are bleached, for example using bleaching earth or active charcoal. At the end, the product is deodorized, for example by using steam.

The term "oil" or "fat" means a fatty acid mixture which comprises unsaturated, saturated, preferably esterified fatty acid(s). It is preferred that the oil or fat has a high content of unsaturated, unconjugated esterified fatty acid(s), in particular linoleic acid, γ-linolenic acid, dihomo-γ-linolenic acid, arachidonic acid, α-linolenic acid, stearidonic acid, eicosatetraenoic acid or eicosapentaenoic acid. The amount of unsaturated esterified fatty acids is preferably approximately 30%, with an amount of 50% being more preferred and an amount of 60%, 70%, 80% or more being even more preferred. For identification purposes, it is possible, for example, to determine the amount of fatty acid by gas chromatography after converting the fatty acids into the methyl esters by means of transesterification. The oil or fat can comprise various other saturated or unsaturated fatty acids. The amount of the various fatty acids in oil or fat can vary in particular as a function of the original plant.

The polyunsaturated fatty acids which are present can be liberated from the compounds of the general formula I produced thus in the process of the invention for example via treatment with alkali, for example aqueous KOH or NaOH, or acid hydrolysis, advantageously in the presence of an alcohol such as methanol or ethanol, or via enzymatic cleavage and isolated via, for example, phase separation and subsequent acidification with, for example, $H_2SO_4$. The fatty acids can also be liberated directly without the above-described processing.

A further embodiment of the invention is the use of the transgenic plant or of the products obtained from said plants in feedstuffs, foodstuffs, seeds, fine chemicals, cosmetics or pharmaceuticals.

The invention further relates to a nucleic acid construct for stable transgenic expression of nucleic acids in the aforementioned process of the invention, comprising
a) a promoter according to SEQ ID NO: 1 or
b) functional equivalents or equivalent fragments which have essentially the same promoter activities as a),
with a) or b) being functionally linked to a nucleic acid sequence to be expressed transgenically.

The nucleic acid construct advantageously comprises at least one further element selected from the following group:
a) the nucleic acid sequence to be expressed being functionally linked to further genetic control sequences, or
b) the nucleic acid construct comprising additional functional elements, or
c) a polylinker being located between the promoter and the nucleic acid sequence to be expressed, or
d) the nucleic acid construct comprising at least one further nucleic acid under the control of the promoter according to SEQ ID NO: 1 or of a functional equivalent or equivalent fragment or of a further promoter.

The nucleic acid construct is advantageously integrated into the genome of the transgenic plant by inserting said nucleic acid construct between two T-DNA sections (=T-DNA borders).

T-DNA sections (=T-DNA borders) are understood by the skilled worker as being a section which enables DNA to be transferred into a plant. The T-DNA has a "right" and a "left" T-DNA border which mediates transfer of the region located between said borders. Important to this transfer are two virtually identical sequences of approx. 25 bp in length (right and left T-DNA borders) which flank the T-DNA on the Ti plasmid and which are recognized by a Ti plasmid-encoded nuclease. Said nuclease is capable of excising a T-DNA single strand from the plasmid, which strand is then stably inserted at a random site into the plant genome. Thus it is possible to insert any nucleic acid sequences into the plant genome.

The nucleic acid sequence to be expressed transgenically in the nucleic acid construct is selected from the group of nucleic acids consisting of a selection marker, a reporter gene, an RNAi construct, an enzyme, a protein which mediates resistance to insects, viruses, bacteria, fungi or nematodes, a nucleic acid sequence or a protein which mediates in plants resistance to drought, cold, heat or salt, an inhibitor, a lectin, an RNAase, a ribozyme, an antibody, a vaccine, a pharmaceutical, an anti-freezing protein, a cytochrome P-450 protein, a transcription activator or repressor or a protein involved in the biosynthesis of fine chemicals.

After having been introduced into a plant cell or plant, the nucleic acids or nucleic acid constructs used in the process are stably integrated into the genome of the host cell. Integration into the genome may be random or may be carried out by recombination in such a way that the native gene is replaced by the introduced copy, thereby modulating production of the desired compound by the cell, or by using a gene in trans so that the gene is functionally linked to a functional expressions unit which comprises at least one sequence ensuring expression of a gene and at least one sequence ensuring the polyadenylation of a functionally transcribed gene. Advantageously, the nucleic acids are transported into the plants in a nucleic acid construct in the form of multiexpression cassettes or constructs for multiparallel expression of genes.

As described above, the present invention aims at integrating nucleic acids or the codogenic gene sections into the genome of the plants. In this context, a particular codogenic gene section may be integrated as a continuous coding sequence (ORF) or may include one or more introns. In the latter case, such sequences are usually spliced in the course of expression by the plant, it being possible but not necessary for the splicing pattern to correspond to that of the donor organism.

In principle, the nucleic acids may be integrated in the extranuclear genome, for example the plastid genome, of a plant. However, preference is given according to the invention to integration into the nuclear genome.

Preference is given according to the invention to the sequences comprising the heterologous codogenic gene sections being stably integrated into the genome of the plants. This is associated with one or more of the following aspects:
  the number of copies of a particular nucleic acid or of a particular codogenic gene section per cell is essentially constant during the life cycle of a plant;
  the number of copies of a nucleic acid or of a particular codogenic gene section per cell can be determined;
  the nucleic acid or the codogenic gene section is inheritable as a feature of the plant, with nuclear integration according to the rules of Mendel.

The number of integrated copies of a nucleic acid or of a particular codogenic gene section per cell is usually less than 20 and in most cases less than 10. Preference is given according to the invention to plants having cells which comprise about 1 to 5 copies and in particular 1 copy of a nucleic acid or of a particular codogenic gene section. The number of copies per cell may be determined in a manner known per se by means of Southern blot analysis (extraction of the genomic DNA, digestion by restriction enzymes, electrophoretic fractionation, membrane transfer, hybridization with a labeled DNA-specific probe) or quantitative PCR.

According to a particular embodiment of the present invention, the advantageously heterologous nucleic acids or codogenic gene sections are flanked on one side or, preferably, on both sides by T-DNA sequences, in particular by agrobacterial Ti-plasmid sequences, in the genome of the transgenic plants. This is likewise an expression of the stable integration according to the invention of the codogenic gene sections into the genome of the plants.

The nucleic acid construct of the invention may then be inserted into a vector for introduction into the transgenic plant. It may, however, also be introduced directly into the plant.

With the use of cloning vectors in plants and in plant transformation, such as those published in and cited therein: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, editors: Kung and R. Wu, Academic Press, 1993, 15-38; B. Jenes et al., Techniques for Gene Transfer, in: Transgenic Plants, vol. 1, Engineering and Utilization, editors: Kung and R. Wu, Academic Press (1993), 128-143; Potrykus, Annu. Rev. Plant Physiol. Plant Molec. Biol. 42 (1991), 205-225)), it is possible to use the nucleic acids or nucleic acid constructs for genetic modification of a broad spectrum of plants, so that said plant becomes a better or more efficient producer of one or more of the aforementioned products. This improved production or efficiency of production may be caused by a direct effect of the manipulation or an indirect effect of said manipulation.

The nucleic acid sequences used in the process are advantageously introduced in the process into the plant in the form of a nucleic acid construct which makes possible stable expression of the nucleic acids in plants.

SEQ ID NO: 2 to 6 depict advantageous promoter/terminator constructs in pUC19, which may be used for construction of the nucleic acid constructs (=expression construct=gene construct). In this context, nucleic acids, for example the nucleic acid sequences coding for the desaturases used in the preparation of PUFAS or for the elongases, are functionally linked to one or more regulatory signals, advantageously for increasing gene expression. The aforementioned ubiquitin promoter may be used in these constructs advantageously instead of one or of all of the indicated and present promoters or in combination with the promoters mentioned or other promoters. These regulatory sequences should make possible specific expression of the genes and protein expression. Depending on the host organism, this may mean, for example, that the gene is expressed and/or overexpressed only after induction or that it is expressed and/or overexpressed immediately. These regulatory sequences are, for example, sequences to which the inducers or repressors bind and thus regulate expression of the nucleic acid. In addition to these new regulatory sequences or instead of these sequences, the natural regulation of said sequences may still be present upstream of the actual structural genes and, where appropriate, may have been genetically modified so that the natural regulation has been switched off and expression of the genes has been increased. The gene construct moreover may also advantageously comprise one or more "enhancer sequences" functionally linked to the promoter, which make possible increased expression of the nucleic acid sequence. Additional advantageous sequences such as further regulatory elements or terminators may also be inserted at the 3' end of the DNA sequences. The nucleic acids to be expressed may be present in the expression cassette (=gene construct) in the form of one or more copies. Advantageously, only one copy of the genes is present in each case in the expression cassette. This gene construct or gene constructs may be expressed together in the host organism. It is advantageous for the insertion of further genes in the host genome, if the genes to be expressed are present together in a gene construct.

The aforementioned promoter/terminator constructs advantageously consist of least two functional units such as a promoter and a terminator. In addition to the nucleic acid to be expressed in the process, further desired gene sequences such as targeting sequences, coding regions of further genes or parts thereof and the like can be inserted between promoter and terminator. To construct expression cassettes, promoters and terminators (USP promoter: Baeumlein et al., Mol Gen Genet, 1991, 225 (3):459-67); OCS terminator: Gielen et al. EMBO J. 3 (1984) 835ff.) are isolated with the aid of the polymerase chain reaction and tailor-made with flanking sequences of choice on the basis of synthetic oligonucleotides.

Examples of oligonucleotides which can be used are the following:

```
USP1 upstream:    CCGGAATTCGGCGCGCCGAGCTCCTCGAGCAAAT
                  TTACACATTGCCA (SEQ ID NO: 7)

USP2 upstream:    CCGGAATTCGGCGCGCCGAGCTCCTCGAGCAAAT
                  TTACACATTGCCA (SEQ ID NO: 8)

USP3 upstream:    CCGGAATTCGGCGCGCCGAGCTCCTCGAGCAAAT
                  TTACACATTGCCA (SEQ ID NO: 9)

USP1 downstream:  AAAACTGCAGGCGGCCGCCCACCGCGGTGGGCTG
                  GCTATGAAGAAATT (SEQ ID NO: 10)

USP2 downstream:  CGCGGATCCGCTGGCTATGAAGAAATT (SE-
                  Q ID
                  NO: 11)

USP3 downstream:  TCCCCCGGGATCGATGCCGGCAGATCTGCTGGCT
                  ATGAAGAAATT (SEQ ID NO: 12)

OCS1 upstream:    AAAACTGCAGTCTAGAAGGCCTCCTGCTTTAATG
                  AGATAT (SEQ ID NO: 13)

OCS2 upstream:    CGCGGATCCGATATCGGGCCCGCTAGCGTTAACC
                  CTGCTTTAATGAGATAT (SEQ ID NO: 14)

OCS3 upstream:    TCCCCCGGGCCATGGCCTGCTTTAATGAGATAT
                  (SEQ ID NO: 15)

OCS1 downstream:  CCCAAGCTTGGCGCGCCGAGCTCGAATTCGTCGA
                  CGGACAATCAGTAAATTGA (SEQ ID NO: 16)

OCS2 downstream:  CCCAAGCTTGGCGCGCCGAGCTCGAATTCGTCGA
                  CGGACAATCAGTAAATTGA (SEQ ID NO: 17)

OCS3 downstream:  CCCAAGCTTGGCGCGCCGAGCTCGTCGACGGACA
                  ATCAGTAAATTGA (SEQ ID NO: 18)
```

The methods are known to the specialist worker and are generally known from the literature.

In a first step, a promoter and a terminator are amplified via PCR. Then, the terminator is cloned into a recipient plasmid and, in a second step, the promoter is inserted upstream of the terminator. This gives an expression cassette on a plasmid vehicle, it being possible to use here advantageously pUC19, although it is also possible to use any other familiar vector.

The promoter/terminator constructs are depicted in SEQ ID NO: 2 to 6 (pUT1=SEQ ID NO: 2, pUT2=SEQ ID NO: 3, pUT3=SEQ ID NO: 4, pUT12=SEQ ID NO: 5, pUT123=SEQ ID NO: 6). They comprise, for example, the USP promoter and the OCS terminator. On the basis of these plasmids, it is possible to prepare in a manner known to the skilled worker nucleic acid constructs which comprise the nucleic acids to be expressed. In this manner, a set of multi-expression cassettes is generated which can be utilized for inserting desired nucleic acids and is described in table 1 and may moreover incorporate still further expression cassettes.

They comprise the following elements:

TABLE 1

| PUC19 derivate | Cleavage sites before the USP promoter | Multiple cloning cleavage sites | Cleavage sites behind the OCS terminator |
|---|---|---|---|
| pUT1 | EcoRI/AscI/SacI/XhoI | BstXI/NotI/PstI/XbaI/StuI | SalI/EcoRI/SacI/AscI/HindIII |
| pUT2 | EcoRI/AscI/SacI/XhoI | BamHI/EcoRV/ApaI/NheI/HpaI | SalI/EcoRI/SacI/AscI/HindIII |

TABLE 1-continued

| PUC19 derivate | Cleavage sites before the USP promoter | Multiple cloning cleavage sites | Cleavage sites behind the OCS terminator |
|---|---|---|---|
| PUT3 | EcoRI/AscI/ SacI/XhoI | BglII/NaeI/ClaI/ SmaI/NcoI | SalI/SacI/AscI/ HindIII |
| pUT12 Double expression cassette | EcoRI/AscI/ SacI/XhoI | BstXI/NotI/PstI/ XbaI/StuI and BamHI/EcoRV/ApaI/ NheI/HpaI | SalI/EcoRI/SacI/ AscI/HindIII |
| pUT123 Triple expression cassette | EcoRI/AscI/ SacI/XhoI | 1. BstXI/NotI/ PstI/XbaI/StuI and 2. BamHI/EcoRV/ ApaI/NheI/HpaI and 3. BglII/NaeI/ ClaI/SmaI/NcoI | SalI/SacI/AscI/ HindIII |

Furthermore, further multiexpression cassettes can be generated and employed for seed-specific gene expression, as described and as specified in greater detail in Table 2, with the aid of the
i) USP promoter or with the aid of the
ii) 700 base pair 3' fragment of the LeB4 promoter or with the aid of the
iii) DC3 promoter.

The DC3 promoter is described in Thomas, Plant Cell 1996, 263:359-368 and consists merely of the region −117 to +26, which is why it therefore constitutes one of the smallest known seed-specific promoters. The expression cassettes can comprise several copies of the same promoter or else be constructed via three different promoters.

TABLE 2

Multiple expression cassettes

| Plasmid name of the pUC19 derivative | Cleavage sites before the respective promoter | Multiple cloning cleavage sites | Cleavage sites behind the OCS terminator |
|---|---|---|---|
| PUT1 (pUC19 with USP-OCS1) | EcoRI/AscI/ SacI/XhoI | (1) BstXI/NotI/ PstI/XbaI/StuI | SalI/EcoRI/SacI/ AscI/HindIII |
| PDCT (pUC19 with DC3-OCS) | EcoRI/AscI/ SacI/XhoI | (2) BamHI/EcoRV/ ApaI/NheI/HpaI | SalI/EcoRI/SacI/ AscI/HindIII |
| PleBT (pUC19-with LeB4(700)-OCS) | EcoRI/AscI/ SacI/XhoI | (3) BglII/NaeI/ ClaI/SmaI/NcoI | SalI/SacI/AscI/ HindIII |
| PUD12 (pUC 19 with USP-OCS1 and with DC3-OCS) | EcoRI/AscI/ SacI/XhoI | (1) BstXI/NotI/ PstI/XbaI/StuI und (2) BamHI/EcoRV/ ApaI/NheI/HpaI | SalI/EcoRI/SacI/ AscI/HindIII |
| PUDL123 Triple expression cassette (pUC19 with USP/DC3 and LeB4-700) | EcoRI/AscI/ SacI/XhoI | (1) BstXI/NotI/ PstI/XbaI/StuI und (2) BamHI/ (EcoRV*)/ApaI/ NheI/HpaI and (3) BglII/NaeI/ ClaI/SmaI/NcoI | SalI/SacI/AscI/ HindIII |

*EcoRV cleavage site, cleaves in the 700 base-pair fragment of the LeB4 promoter (LeB4-700)

Further promoters for multi-gene constructs can be generated analogously, in particular using the
a) ubiquitin promotor used in the process of the invention (see SEQ ID NO: 1) and/or
b) 2.7 kB fragment of the LeB4 promoter and/or
c) phaseolin promoter and/or
d) constitutive v-ATPase c1 promoter.

It may be furthermore desirable to use further suitable promoters for constructing seed-specific multi-expression cassettes such as, for example, the napin promoter or the arcelin-5 promoter.

In this context, the additional regulatory sequences or factors advantageously present in the nucleic acid construct may, as described above, positively influence and thus increase preferably gene expression of the introduced genes. Thus the regulatory elements may advantageously be enhanced at the transcriptional level by using strong transcription signals such as promoters and/or enhancers. In addition to this, however, it is also possible to enhance translation, for example by improving the stability of mRNA.

In this context, the regulatory sequences or factors can, as described above, preferably have a positive effect on the gene expression of the genes which have been introduced, thus enhancing it. Thus, the regulatory elements can advantageously be enhanced at transcriptional level by using strong transcription signals such as promoters and/or enhancers. In addition, however, an enhancement of translation is also possible, for example by improving the stability of the mRNA.

Genetic regulatory sequences furthermore also comprise the 5' untranslated region, introns or the noncoding 3' region of genes. It has been shown, that these may play a significant function in the regulation of gene expression. Thus, 5' untranslated sequences have been shown to be able to enhance transiently and advantageously stable expression of heterologous genes.

Advantageous further regulatory sequences for the novel process, which may additionally be present in the nucleic acid construct, are present, for example, in promoters such as the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Also advantageous in this connection are inducible promoters such as the promoters described in EP-A-0 388 186 (benzylsulfonamide-inducible), Plant J. 2, 1992: 397-404 (Gatz et al., tetracycline-inducible), EP-A-0 335 528 (abscisic acid-inducible) or WO 93/21334 (ethanol- or cyclohexenol-inducible). Further useful plant promoters are the potato cytosolic FBPase promoter or ST-LSI promoter (Stockhaus et al., EMBO J. 8, 1989, 2445), the glycine max phosphoribosyl-pyrophosphate amidotransferase promoter (Genbank Accession No. U87999) or the node-specific promoter described in EP-A-0 249 676. Advantageous promoters are also seed-specific promoters, such as the USP promoter in accordance with the specification, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis* oleosin promotor), U.S. Pat. No. 5,504,200 (*Phaseolus vulgaris* phaseolin promoter), WO 91/13980 (*Brassica* Bce4 promoter) described by Baeumlein et al., Plant J., 2, 2, 1992: 233-239 (LeB4 promoter from a legume), said promoters being useful in dicotyledones. The following promoters are suitable for example in monocotyledones: barley lpt-2 or lpt-1 promoter (WO 95/15389 and WO 95/23230), barley hordein promoter and other suitable promoters which are described in WO 99/16890.

In principle, it is possible to use all natural promoters with their regulatory sequences like those mentioned above for the novel process. It is likewise possible and advantageous to use synthetic promoters, in addition or alone, especially when they confer seed-specific expression, such as, for example, described in WO 99/16890.

In principle, further advantageous seed-specific promoters can be isolated from both dicotyledonous and monocotyledonous plant. Advantageous preferred promoters are detailed hereinbelow: USP (=unknown seed protein) and vicilin (*Vicia faba*) [Bäumlein et al., Mol. Gen Genet., 1991, 225(3)], napin (oilseed rape) [U.S. Pat. No. 5,608,152], acyl-carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legume B4 (LegB4 promoter) [Bäumlein et al., Plant J., 2, 2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or β-amylase (barley) [EP 781 849].

Plant gene expression can also be facilitated via a chemically inducible promoter (see a review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure the stable integration of the nucleic acid constructs into the transgenic plant over a plurality of generations, each of the nucleic acids used in the process should be expressed under the control of a separate promoter, preferably a promoter which differs from the other promoters, since repeating sequence motifs can lead to instability of the T-DNA, or to recombination events or gene silencing. In this context, the expression cassette is advantageously constructed in such a way that a promoter is followed by a suitable cleavage site, advantageously in a polylinker, for insertion of the nucleic acid to be expressed and, if appropriate, a terminator is positioned behind the polylinker. This sequence is repeated several times, preferably three, four or five times, so that up to five genes can be combined in one construct and introduced thus into the transgenic plant in order to be expressed. Advantageously, the sequence is repeated up to three times (see sequence listing SEQ ID NO: 2 to 6). To express the nucleic acid sequences, the latter are inserted after the promoter via the suitable cleavage site, for example in the polylinker. Advantageously, each nucleic acid sequence has its own promoter and, if appropriate, its own terminator. However, it is also possible to insert a plurality of nucleic acid sequences after a promoter and, if appropriate, before a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the parsley ubiquitin promoter, the USP, LegB4 or DC3 promoter, and different terminators can be used in the expression cassette. However, it is also possible to use only one type of promoter in the cassette, which, however, may lead to undesired recombination events.

Homologous recombination for stable integration is a relatively rare event in higher eukaryotes, especially in plants. Random integrations in the host genome predominate. One possibility of removing the randomly integrated sequences and thus concentrating cell clones having a correct homologous recombination is the use of a sequence-specific recombination system, as described in U.S. Pat. No. 6,110,736. Said system consists of three elements: two pairs of specific recombinant sequences and one sequence-specific recombinase. This recombinase catalyzes a recombination only between the two pairs of specific recombinant sequences. One pair of these specific DNA sequences is located outside the DNA sequence to be integrated, i.e. outside the two homologous DNA sequences. In the case of correct homologous recombination, these sequences are not cotransferred into the genome. In the case of random integration, they usually insert together with the rest of the construct. Using a special recombinase and a construct comprising a second pair of the specific sequences, it is possible to excise the randomly inserted sequences or to inactivate them by inversion, while the sequences inserted correctly via homologous recombination remain in the genome. A multiplicity of sequence-specific recombination systems may be used, and mention is made by way of example of the Cre/lox system of bacteriophage P1, the yeast FLP/FRT system, the Gin recombinase of phage Mu, the *E. coli* Pin recombinase and the R/RS system of the pSR1 plasmid. Preference is given to the bacteriophage P1 Cre/lox and the yeast FLP/FRT systems. Here, the recombinase (Cre or FLP) interacts specifically with its particular recombinant sequences (34 bp lox sequence and 47 bp FRT sequence, respectively), in order to delete or invert the sequences stored in between. The FLP/FRT and cre/lox recombinase systems have already been used in plant systems (Odell et al., Mol. Gen. Genet., 223:369-378, 1990.)

As described above, the transcription of the genes which have been introduced should advantageously be terminated by suitable terminators at the 3' end of the biosynthesis genes which have been introduced (after the stop codon). An example of a sequence which can be used in this context is the OCS1 terminator. As is the case with the promoters, different terminators should be used for each gene.

The nucleic acid construct may advantageously comprise one or more "enhancer sequences" functionally linked to the promoter, which make possible increased transgenic expression of the nucleic acid sequence. It is also possible to insert additional advantageous sequences such as further regulatory elements or terminators at the 3' end of the nucleic acid sequences to be expressed transgenically. The gene construct may contain one or more copies of the nucleic acid sequences to be expressed transgenically.

Control sequences mean furthermore those sequences which enable homologous recombination or insertion into the genome of a host organism or allow removal from the genome. Homologous recombination may involve, for example, replacing the natural promoter of a particular gene with the nucleic acid sequence to be expressed and/or the promoter. Methods such as the cre/lox technique allow tissue-specific, possibly inducible removal of the expression cassette from the genome of the host organism (Sauer B. Methods. 1998; 14(4):381-92). Here, particular flanking sequences (lox sequences) may be attached to the target gene, which later enable a removal by means of the cre recombinase.

As described above, the nucleic acid construct can also comprise further genes to be introduced into the organisms. It is possible and advantageous to introduce into the host organisms, and to express therein, regulatory genes such as genes for inducers, repressors or enzymes which, owing to their enzyme activity, engage in the regulation of one or more genes of a biosynthesis pathway. These genes can be of heterologous or of homologous origin. Moreover, further biosynthesis genes of the fatty acid or lipid metabolism can advantageously be present in the nucleic acid construct, or gene construct; however, these genes can also be present on one or more further nucleic acid constructs. In the case of the fatty acid or lipid metabolism, the biosynthesis gene used are advantageously a gene selected from the group acyl-CoA dehydrogenase(s), acyl-ACP [=acyl carrier protein] desaturase(s), acyl-ACP thioesterase(s), fatty acid acyl transferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s) or their combinations.

In this context, the abovementioned desaturases can be cloned into nucleic acid constructs of the invention in combination with elongases and other desaturases and employed for the transformation of plants with the aid of *Agrobacterium*. Other transformation methods are the protoplast polyethylene glycol (PEG) method, the protoplast electroporation, the protoplast microinjection or the ballistic methods.

Selection of successfully homologously recombined or else transformed cells usually requires to additionally introduce into the nucleic acid construct a selectable marker which imparts to the successfully recombined cells, for example, a resistance to a biocide (for example a herbicide), a metabolism inhibitor such as 2-deoxyglucose 6-phosphate (WO 98/45456) or an antibiotic. The selection marker allows the transformed cells to be selected from the untransformed cells (McCormick et al., Plant Cell Reports 5 (1986), 81-84).

Further examples of selection markers are selectable markers such as biocides such as phosphinotricin, glyphosate, sulfonylurea and imidazolinone or bromoxynil; metabolism inhibitor such as 2-deoxyglucose 6-phosphate or antibiotics such as kanamycin, G 418, bleomycin, hygromycin.

In addition to the aforementioned selection markers, it is also possible to express in the process of the invention advantageously pathogen resistance genes such as genes of resistance to insects, fungi, bacteria and/or viruses. Said genes should be expressed as uniformly as possible within the plant and/or plant tissues.

Suitable selection markers are also metabolism inhibitors such as 2-deoxyglucose 6-phosphate (WO 98/45456).

Advantageous further genes in the nucleic acid construct are reporter genes which encode readily quantifiable proteins and which ensure, via intrinsic color or enzyme activity, evaluation of the transformation efficiency, the site or time of expression. Very particular preference is given here to genes encoding reporter proteins (see also Schenborn E, Groskreutz D. Mol Biotechnol. 1999; 13(1):29-44) such as green fluorescence protein (GFP) [Chui W L et al., Curr Biol 1996, 6:325-330; Leffel S M et al., Biotechniques. 23(5):912-8, 1997; Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12): 5888-5893; Tian et al. (1997) Plant Cell Rep 16:267-271; WO 97/41228], chloramphenicol transferase, luciferase [Millar et al., Plant Mol Biol Rep 1992 10:324-414; Ow et al. (1986) Science, 234:856-859] which allows bioluminescence detection; β-galactosidase coding for an enzyme for which various chromogenic substrates are available which are less preferred in plants, owing to a high basic activity; β-glucuronidase (GUS) [Jefferson et al., EMBO J. 1987, 6, 3901-3907, uidA gene] which encodes an enzyme for various chromogenic substrates. Further examples of genes are xylE, alpha-amylase, tyrosinase or aequorin.

Further advantageous genes are genes for enzymes such as oxidoreductases, transferases, hydrolases, lyases, isomerases or ligases, preferred enzymes being the hydrolases.

Genes for pharmaceuticals such as those for insulin or for the various mediators such as EPO or interferons, may also be included.

In this context, the regulatory sequences or factors can, as described above, preferably have a positive effect on the gene expression of the genes which have been introduced, thus enhancing it. Thus, the regulatory elements can advantageously be enhanced at the transcriptional level by using strong transcription signals such as promoters and/or enhancers. In addition, however, an enhancement of translation is also possible, for example by improving the stability of the mRNA. In principle, the expression cassettes can be used directly for introduction into the plant, or else be introduced into a vectors.

These advantageous vectors, preferably expression vectors, comprise the nucleic acid constructs used in the process, which the nucleic acids used comprise alone or in combination with further genes. As used in the present context, the term "vector" refers to a nucleic acid molecule which is capable of transporting another nucleic acid, to which it is bound. One type of vector is a "plasmid", which represents a circular double-stranded DNA loop into which additional DNA segments can be ligated. Another type of vector is a viral vector, it being possible for additional DNA segments to be ligated in the viral genome. Certain vectors are capable of autonomous replication in a host cell into which they have been introduced (for example bacterial vectors with bacterial origin of replication). Other vectors are advantageously integrated in the genome of a host cell when being introduced into the host cell, whereby they replicate together with the host genome. Moreover, certain vectors are capable of governing the expression of genes with which they are operably linked. These vectors are referred to herein as "expression vectors". Usually, expression vectors which are suitable for DNA recombination techniques take the form of plasmids. In the present description, "plasmid" and "vector" can be used interchangeably since the plasmid is the most frequently used vector form. However the invention is also intended to comprise these other forms of expression vectors, such as viral vectors, which have similar functions. Furthermore, the term vector is also intended to comprise other vectors which are known to the skilled worker, such as phages, viruses such as SV40, CMV, TMV, transposons, IS elements, phasmids, phagemids, cosmids, linear or circular DNA.

The recombinant nucleic acid constructs which are advantageously used in the process and which are suitable for stable expression in a host cell of the nucleic acids used comprise one or more regulatory sequences selected on the basis of the host cells to be used for the expression, which is linked operably with the nucleic acid sequence to be expressed. "Linked operably" in a recombinant nucleic acid construct or vector means that the nucleotide sequence of interest is bound to the regulatory sequence(s) in such a way that the expression of the nucleotide sequence is possible and that they are bound with one another so that both sequences fulfill the predicted function ascribed to the sequence (for example in an in-vitro transcription/translation system or in a host cell if the vector is introduced into the host cell). The term "regulatory sequence" is intended to comprise promoters, enhancers and other expression control elements (for example polyadenylation signals). These regulatory sequences are described for example in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., eds.: Glick and Thompson, chapter 7, 89-108, including the references therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of the host cell to be transformed, the expression level of the desired protein and the like.

The recombinant nucleic acid constructs and vectors used can be employed for stable expression in algae (Falciatore et al., 1999, Marine Biotechnology. 1, 3:239-251) and preferably in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.:583-586; Plant Molecular Biology and Biotechnology, C Press, Boca Raton, Fla., chapter 6/7, pp. 71-119 (1993); F. F. White, B. Jenes et al., Techniques for Gene Transfer, in: Transgenic Plants, vol. 1, Engineering and Utilization, ed.: Kung and R. Wu, Academic Press (1993), 128-43; Potrykus, Annu. Rev. Plant Physiol. Plant Molec. Biol. 42 (1991), 205-225 (and references cited therein)), according to the methods mentioned above.

In a further embodiment of the process, the nucleic acid sequences used can be expressed in single-cell plant cells (such as algae), see Falciatore et al., 1999, Marine Biotechnology 1 (3):239-251 and references cited therein, and plant cells from higher plants (for example spermatophytes such as crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, vol. 1, Engineering and Utilization, ed.: Kung and R. Wu, Academic Press, 1993, pp. 15-38.

A plant expression cassette preferably comprises regulatory sequences which are capable of governing the gene expression in plant cells and which are linked operably so that each sequence can fulfill its function, such as transcription or termination, for example polyadenylation signals. Preferred polyadenylation signals are those which originate from *Agrobacterium tumefaciens* t-DNA, such as the gene 3 of the Ti plasmid pTiACH5, which is known as octopine synthase (Gielen et al., EMBO J. 3 (1984) 835ff.) or functional equivalents thereof, but all other terminators which are functionally active in plants are also suitable.

Since plant gene expression is very often not limited to the transcriptional levels, a plant expression cassette preferably comprises other operably linked sequences such as translation enhancers, for example the overdrive sequence which comprises the 5'-untranslated leader sequence from tobacco mosaic virus, which increases the protein/RNA ratio (Gallie et al., 1987, Nucl. Acids Research 15:8693-8711).

As described above, plant gene expression must be linked operably with a suitable promoter which performs gene expression with the correct timing or in a cell- or tissue-specific manner. Utilizable promoters are constitutive promoters (Benfey et al., EMBO J. 8 (1989) 2195-2202) such as those which are derived from plant viruses, such as 35S CAMV (Franck et al., Cell 21 (1980) 285-294), 19S CaMV (see also U.S. Pat. No. 5,352,605 and WO 84/02913) or plant promoters such as that of the Rubisco small subunit, which is described in U.S. Pat. No. 4,962,028. These may advantageously be combined with the parsley ubiquitin promoter in the process of the invention.

Other sequences which are preferred for the use for operable linkage in plant gene expression cassettes are targeting sequences, which are required for targeting the gene product into its relevant cell compartment (for a review see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other plant cell compartments.

Plant gene expression can also be facilitated as described above via a chemically inducible promoter (for a review see Gatz 1997, Annu. Rev. Plant Physiol. Plant Mol. Biol., 48:89-108). Chemically inducible promoters are suitable in particular when it is desired that gene expression is clock-specific. Examples of such promoters are a salicylic acid-inducible promoter (WO 95/19443), a tetracycline-inducible promoter (Gatz et al. (1992) Plant J. 2, 397-404) and an ethanol-inducible promoter.

Other promoters which are suitable are promoters which respond to biotic or abiotic stress conditions, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Preferred promoters are in particular those additional ones which bring about the expression of genes in tissues and organs in which lipid and oil biosynthesis takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504, 200), the *Brassica* Bce4 promoter (WO 91/13980) or the legumin B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable promoters which should be taken into consideration are the barley lpt2 or lpt1 gene promoter (WO 95/15389 and WO 95/23230), or those described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene).

In particular, it may be desired to bring about the multiparallel expression of the nucleic acid sequences used in the process alone or in combination with other genes. Such expression cassettes can be introduced via the simultaneous transformation of a plurality of individual expression constructs or, preferably, by combining a plurality of expression cassettes on one construct. Also, it is possible to transform a plurality of vectors with in each case a plurality of expression cassettes and to transfer them to the host cell.

Promoters which are likewise especially suitable are those which bring about the plastid-specific expression since plastids are the compartment in which the precursors and some end products of lipid biosynthesis are synthetized. Suitable promoters such as the viral RNA polymerase promoter are described in WO 95/16783 and WO 97/06250, and the *Arabidopsis* clpP promoter, described in WO 99/46394.

The nucleic acid constructs or vectors can be introduced into plants via conventional transformation techniques. The term "transformation", as used in the present context, is meant to comprise a multiplicity of methods known in the art for introducing foreign nucleic acid (for example DNA) into a host cell, including chemically mediated transfer, electroporation or particle bombardment. Suitable methods for the transformation or transfection of host cells, including plant cells, can be found in Sambrook et al. (Molecular Cloning: A Laboratory Manual., 2nd edition., Cold Spring Harbor Laboratory, Cold Spring Harbor Laboratory Press, Cold Spring Harbor, N.Y., 1989) and other laboratory handbooks such as Methods in Molecular Biology, 1995, vol. 44, *Agrobacterium* protocols, ed.: Gartland and Davey, Humana Press, Totowa, N.J.

Host cells which are suitable in principle for taking up the nucleic acid, the nucleic acid construct of the invention or the vector of the invention are all plants or parts thereof, preference being given to dicotyledonous or monocotyledonous plants such as oilseed rape, evening primrose, hemp, thistle, peanut, canola, linseed, soya, safflower, sunflower, borage or plants such as maize, wheat, rye, oats, triticale, rice, barley, cotton, manioc, pepper, *tagetes*, Solanaceae plants such as potato, tobacco, eggplant and tomato, *Vicia* species, pea, alfalfa, bush plants (coffee, cocoa, tea), *Salix* species, trees (oil palm, coconut) and perennial grasses and fodder crops. Especially preferred transgenic plants of the invention are selected from the group consisting of corn, rice, triticale, wheat, rye, barley, oats, rye grass, millet, oilseed rape, evening primrose, canola, peanut, verbascum, thistle, hazelnut, almond, macadamia, avocado, bay, wild roses, pumpkin, pistachios, sesame, linseed, sunflower, safflower, soybean, borage, poppy, mustard, hemp, castor-oil plant, olive, calendula, punica, sugar beet, tomato, potato, tobacco, carrot, poplar, cotton, manioc, pepper, *tagetes*, eggplant, pea, alfalfa, coffee, cocoa, tea, oil palm, coconut, walnut or *Arabidopsis*.

The promoter advantageously used in the process and having the nucleotide sequence SEQ ID NO: 1, a functional equivalent or an equivalent fragment may be isolated using standard molecular-biological techniques and the sequence information provided here. It is also possible to identify with the aid of comparative algorithms, for example, a homologous sequence or homologous, conserved sequence regions at the DNA or amino acid level. These may be used as hybridization probe and standard hybridization techniques (as described, for example, in Sambrook et al., Molecular Cloning: A Laboratory Manual. 2nd edition, Cold Spring Harbor Laboratory, Cold Spring Harbor Laboratory Press, Cold Spring Harbor, N.Y., 1989) for isolating further promoter sequences useful in the process. In addition, it is possible to isolate a nucleic acid molecule comprising a complete sequence of SEQ ID NO: 1 or a part thereof by polymerase chain reaction, using oligonucleotide primers on the basis of said sequence or of parts thereof (for example, a nucleic acid molecule comprising the complete sequence or a part thereof may be isolated by polymerase chain reaction using oligonucleotide primers which have been generated on the basis of said same sequence). Methods of isolating genomic DNA from plants are known to the skilled worker.

Promoters which are advantageous for the process according to the invention can be isolated on the basis of their homology with nucleic acids disclosed herein using the sequences or part thereof as hybridization probe, following standard hybridization techniques under stringent hybridization conditions. In this context, it is possible for example to use isolated nucleic acid molecules which are at least 18 nucleotides in length and which hybridize under stringent conditions with the nucleic acid molecules which comprise a nucleotide sequence of SEQ ID NO: 1. Advantageously, it is also possible to use nucleic acids with at least 25, 50, 100, 250 or more nucleotides. The term "hybridizes under stringent conditions" as used in the present context is understood as describing hybridization and wash conditions under which nucleotide sequences with at least 60% homology with one another usually remain hybridized with one another. The conditions are preferably such that sequences which are at least approximately 65%, more preferably at least approximately 70% and even more preferably at least approximately 75% or more homologous with one another usually remain hybridized with one another. These stringent conditions are known to the skilled worker and can be found in Current Protocols in Molecular Biology, John Wiley & Sons, N.Y. (1989), 6.3.1-6.3.6. A preferred nonlimiting example of stringent hybridization conditions is hybridization in 6× sodium chloride/sodium citrate (SSC) at approximately 45° C., followed by one or more wash steps in 0.2×SSC, 0.1% SDS at 50 to 65° C. The skilled worker knows that these hybridization conditions differ depending on the type of the nucleic acid and, for example when organic solvents are present, with regard to the temperature and concentration of the buffer. For example, under "standard hybridization conditions" the temperature differs depending on the type of nucleic acid between 42 and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids preferably are for example 0.1×SSC and 20 to 45° C., preferably between 30 and 45° C. The hybridization conditions for DNA:RNA hybrids preferably are for example 0.1×SSC and 30° C. to 55° C., preferably between 45° C. and 55° C. The abovementioned hybridization temperatures are determined for example for a nucleic acid with a length of approximately 100 bp (=base pairs) and a G+C content of 50% in the absence of formamide. The skilled worker knows how to identify the hybridization conditions required with the aid of textbooks, such as the one mentioned above, or the following textbooks: Sambrook et al., "Molecular Cloning", Cold Spring Harbor Laboratory, 1989; Hames and Higgins (ed.) 1985, "Nucleic Acids Hybridization: A Practical Approach", IRL Press at Oxford University Press, Oxford; Brown (ed.) 1991, "Essential Molecular Biology: A Practical Approach", IRL Press at Oxford University Press, Oxford.

To determine the percentage homology (=identity) of two sequences (for example SEQ ID NO: 1), the sequences are written underneath each other to provide an optimal comparison (for example, gaps may be introduced into the sequence of a promoter in order to generate an optimal alignment with the other promoter and its functionally essential elements like the transcription start or the TATA box). The nucleotides at the corresponding nucleotide positions are then compared. If a position in a sequence is occupied by the same nucleotide as the corresponding position in the other sequence, the molecules are homologous at this position (i.e. nucleic acid "homology" as used in the present context thus corresponds to nucleic acid "identity"). The percentage homology between the two sequences is a function of the number of identical positions which the sequences share (i.e. % homology=number of identical positions/total number of positions×100). The terms homology and identity are thus to be regarded as synonymous.

The invention further relates to transgenic plants which contain the nucleic acid construct of the invention or the vector of the invention.

The invention is illustrated further by the examples which follow, but which are not to be construed as limiting. The contents of all of the references, patent applications, patents and published patent applications cited in the present patent application are herein incorporated by reference.

EXAMPLES SECTION

Example 1

Isolation of Genomic DNA from *Petroselinum Crispum* var. Hamburger Schnitt

Leaf material of 3 week old parsley plants var. Hamburger Schnitt was harvested and shock-frozen in liquid nitrogen. 100 mg of material were homogenized in a mortar and genomic DNA (gDNA) was isolated from the homogenate, using the NUCLEOSPIN Plant kit from Macherey and Nagel according to the manufacturer's information. The gDNA was taken up in 100 µl of TE buffer. The concentration was then determined photometrically. The yield was 1.05 µg/µl.

Example 2

Isolation of the Promoter from Genomic DNA by Means of PCR

Oligonucleotides were derived from the sequence having the NCBI accession number X64345.1 [Kawalleck et al., (1993) Polyubiquitin gene expression and structural properties of the ubi4-2 gene in *Petroselinum*. Plant Molecular Biology. 21(4):673-84]. The oligos were derived from the sequence of base pairs 1 to 22 and 982 to 959. To clone the promoter, recognition sequences of restriction enzymes were attached to the oligonucleotides. The sequence of the oligos was as follows:

```
PcUbi4-2fw:                         (SEQ ID NO: 19)
gctctagaattcgaatccaaaaattacg PcUbi4-2rev:                        (SEQ ID NO: 20)
gggctgcacatacataacatatcaaga
```

The oligos were adjusted to a concentration of 20 µM and used in a PCR.

The PCR mixture contained:

5.0 µl of buffer for Pfu polymerase (Stratagene)

0.4 µl of dNTPs (25 mM each) (Amersham)

0.5 µl of primer PcUbi4-2fw 0.5 µl of primer PcUbi4-2rev 0.5 µl of Pfu polymerase (Stratagene)

0.5 µl of gDNA 42.6 µl of water

The program of the PCR reaction (MJ-Cycler Tetrad, BioZym) was as follows:

4 min at 94° C.

1 min at 94° C.

1 min at 50° C.

2 min at 72° C.

10 min at 72° C.

25° C.

The central cycle was repeated 30 times.

Example 3

Cloning of the Promoter PCR Fragment

In order to clone the 982 bp PCR fragment, the PCR mixture was purified using the Qiagen PCR purification kit according to the manufacturer's information. The DNA was subsequently taken up in 30 µl of TE buffer and digested completely with XbaI (MBI-Fermentas). The restriction mixture contained: 30 µl of DNA, 4 µl of water, 4 µl of buffer and 2 µl of enzyme (MBI Fermentas). The incubation was carried out at 37° C. overnight.

After purification, the fragment was cloned into a binary vector containing an expression cassette and uidA as a reporter gene, which vector had been opened previously by the restriction enzymes XbaI, SmaI (MBI Fermentas). This resulted in the construct 1bxPcUbi4-2GUS (FIG. 1) comprising the PcUbi4-2 promoter upstream of the GUS gene which is suitable for promoter analysis [Jefferson et al., (1987) GUS fusions: β-Glucuronidase as a sensitive and versatile gene fusion marker in higher plants. EMBO J. 6, 3901-3907].

Example 4

Transformation of the 1bxPcUbi4-2GUS Construct into *Arabidopsis*

The 1bxPcUbi4-2GUS construct was transformed by means of electroporation into the agrobacterial strain pGV3101 containing the plasmid pMP90, and the colonies were plated on TB medium (QBiogen, Germany) containing the selection markers kanamycin, gentamycin and rifampicin and incubated at 28° C. for 2 days.

A colony was picked from the agar plate with the aid of a toothpick and taken up in 3 ml of liquid TB medium containing the antibiotics mentioned above.

The preculture grew at 28° C. and 120 rpm in a shaker incubator for 48 h. 400 ml of LB medium containing the appropriate antibiotics were used for the main culture. The preculture was transferred to the main culture which grew at 28° C. and 120 rpm for 18 h.

After centrifugation at 4000 rpm, the pellet was resuspended in infiltration medium (M & S medium containing 10% sucrose).

Example 5

Cultivation of Plants

Dishes (Piki Saat 80, green, provided with a screen bottom, 30×20×4.5 cm, from Wiesauplast, Kunststofftechnik, Germany) were half-filled with a GS 90 substrate (standard soil, Werkverband E. V., Germany). The dishes were watered overnight with 0.05% Previcur solution (Previcur N, Aventis CropScience). *Arabidopsis thaliana*, C24 seeds were scattered onto the dish, approx. 1000 seeds per dish. The dishes were covered with a hood and placed in the stratification facility (8 h, 110 µE, 5° C.; 16 h, dark, 6° C). After 5 days, the dishes were placed into the short-day controlled environment chamber (8 h, 130 µE, 22° C.; 16 h, dark, 20° C.), where they remained for 10 days, until the first true leaves had formed.

The seedlings were transferred into pots containing the same 20 substrate (Teku pots, Ø 10 cm, LC series, manufactured by Pöppelmann GmbH & Co, Germany). 9 plants were pricked out into each pot. The pots were then returned into the short-day controlled environment chamber for further growth.

After 10 days, they were then transferred to a greenhouse cabinet, 16 h, 340 µE, 22° C. and 8 h, dark, 20° C. Here, growth was continued for 10 more days.

Example 6

Methods of Transformation 7 week old *Arabidopsis* plants which had just started flowering were immersed into the above-described agrobacterial suspension for 10 s. Said suspension had been admixed previously with 10 µl of SILWET L-77 (Crompton S. A., Osi Specialties, Switzerland). The method is described in Bechtold N. and Pelletier G. [In planta *Agrobacterium*-mediated transformation of adult *Arabidopsis thaliana* plants by vacuum infiltration. Methods in Molecular Biology, 82:259-66, 1998]. The plants were subsequently placed into a humid chamber for 18 h, and thereafter the pots were returned to the greenhouse for further growth. Here the plants remained for 10 more weeks, until the seeds were harvested.

Example 7

Selection

Depending on the resistance marker used for selecting the transformed plants, the harvested seeds were planted in the greenhouse and subjected to a spray selection or else, after sterilization, grown on agar plates containing the respective selection agent. After approx. 10 to 14 days, the transformed resistant plants differed markedly from the wild-type seedlings which had died, and were pricked into 6 cm pots.

Example 8

Qualitative Determination of GUS Activity in Tissues of Transgenic *Arabidopsis* Plants Transgenic *Arabidopsis* plants were pricked out and cultivated in the greenhouse. At various points in time, samples were taken from different tissues. These samples were used to carry out GUS stainings [Martin et al., (1992) The GUS reporter system as a tool to study plant gene expression. In: Gallagher (editor): GUS Protocols: Using the GUS gene as a reporter of gene expression. Academic Press, 23-43], in order to investigate in which tissues the PcUbi4-2 promoter is active. For comparison, plants were analyzed which contained in the same vector the double 35S promoter (d35S) upstream of the GUS gene [Kay et al,. 1987, Science, 236, 1299-1302]. Said promoter is a constitutive promoter which has been characterized very well previously [Comai et al., 1990, Plant Molecular Biology 15, 373-381, 1990].

In leaves of 3 week old individual, independent plants, strong, uniform staining of all tissues was observed (FIG. 2). In comparison therewith, the leaves of the plants transformed with d35S:GUS had a very variable staining and partially exhibited a speckled staining pattern (FIG. 3). d35S exhibited hardly any activity in seeds, whereas PcUbi4-2 had strong activity (FIG. 7).

Example 9

Quantitative Determination of the Amount of GUS mRNA in Leaves of Transgenic *Arabidopsis* Plants Leaves of 3 week old transgenic *Arabidopsis* plants were harvested and total RNA was extracted using the INVISORB Plant Kit (Invitek, Germany). The RNA was used in order to determine therefrom the amount of GUS mRNA. The reagents for cDNA synthesis and Q-PCR reaction were from Applied Biosystems and used according to the manufacturer's information. The analysis was carried out by quantitative PCR, TAQMAN probes and the ABIPrism7700 (PE Applied Biosystems) [Gibson et al., (1996) A novel method for real time quantitative RT-PCR. Genome Res. 6, 995-1001; Lie Y. S. and Petropulos C. J. (1998) Advances in quantitative PCR technology: 5' nuclease assays].

The following probe system was used for detecting the GUS mRNA:

```
Oligo1:                               (SEQ ID NO: 21)
5' ccatctcataaataacgtcatgcattac 3'

Probe:                                (SEQ ID NO: 22)
5' tgtaaatcatcgcaagaccggcaacag 3'

Oligo2:                               (SEQ ID NO: 23)
5' aacatttggcaataaagtttcttaaga 3'
```

The probe had been labeled with FAM (fluorescein), the quencher was TAMRA (Rhodamine).

In order to normalize the amount of total RNA used, a probe system was used which detects the mRNA of the ubiquitin-conjugating enzyme 18 (Ubi 18):

```
Oligo1:                               (SEQ ID NO: 24)
5' agttcacccgaaaagcaacg 3'

Probe:                                (SEQ ID NO: 25)
5' cccactgataatgatcgatatgtgaagaactgc 3'

Oligo2:                               (SEQ ID NO: 26)
5' tcgtcatggaaccaccacct 3'
```

The probe had been labeled with VIC (tradename), the quencher was TAMRA.

The Ct value for Ubi18 mRNA, determined for each plant, was subtracted from the GUS mRNA Ct value determined from the same reaction mixture. The delta Ct value calculated therefrom is a relative value and a measure for the amount of GUS mRNA present in a particular amount of mRNA (table 3). The Q-PCR is monitored over 40 cycles. Samples which indicate a Ct value of 40 are negative, since, even in cycle 40, they have not developed any fluorescence greater than the background.

Both promoters show expression in a comparable region. However, the variance in the amount of GUS MRNA is lower for the PcUbi4-2 promoter than for d35S. The median of expression in T1 plants expressing GUS under the control of the PcUbi4-2 promoter was 2.25, the range of all plants was 10.47. For the d35S promoter, the median was 2.38, the range was 13.44.

TABLE 3

Ct values for T1 plants containing the constructs D35S35SGUS or PcUbi4-2GUS.

| Sample Name | Ct GUS | Ct Ubi18 | deltaCt | Sample Name | Ct GUS | Ct Ubi18 | deltaCt |
|---|---|---|---|---|---|---|---|
| D35S1 | 31.15 | 28.47 | 2.68 | PcUbi1 | 34.88 | 29.18 | 5.70 |
| D35S2 | 30.21 | 27.46 | 2.75 | PcUbi2 | 31.54 | 29.57 | 1.97 |
| D35S3 | 29.18 | 27.11 | 2.07 | PcUbi3 | 31.39 | 28.99 | 2.40 |
| D35S4 | 29.40 | 27.39 | 2.02 | PcUbi4 | 32.98 | 29.36 | 3.62 |
| D35S5 | 28.78 | 27.32 | 1.46 | PcUbi5 | 32.95 | 28.79 | 4.16 |
| D35S6 | 28.35 | 28.19 | 0.15 | PcUbi6 | 32.57 | 28.96 | 3.62 |
| D35S7 | 32.03 | 29.04 | 2.99 | PcUbi7 | 34.60 | 29.51 | 5.10 |
| D35S8 | 30.72 | 28.39 | 2.33 | PcUbi8 | 33.09 | 27.67 | 5.42 |

TABLE 3-continued

Ct values for T1 plants containing the constructs D35S35SGUS or PcUbi4-2GUS.

| Sample Name | Ct GUS | Ct Ubi18 | deltaCt | Sample Name | Ct GUS | Ct Ubi18 | deltaCt |
|---|---|---|---|---|---|---|---|
| D35S9 | 31.28 | 28.37 | 2.92 | PcUbi9 | 32.47 | 29.41 | 3.07 |
| D35S10 | 30.30 | 28.07 | 2.23 | PcUbi10 | 34.34 | 29.16 | 5.18 |
| D35S11 | 31.90 | 28.22 | 3.68 | PcUbi11 | 32.25 | 29.60 | 2.65 |
| D35S12 | 29.73 | 28.33 | 1.41 | PcUbi13 | 34.84 | 29.86 | 4.98 |
| D35S13 | 30.67 | 28.82 | 1.86 | PcUbi14 | 32.63 | 29.95 | 2.69 |
| D35S14 | 33.16 | 28.59 | 4.58 | PcUbi15 | 34.78 | 30.46 | 4.32 |
| D35S15 | 32.40 | 28.11 | 4.29 | PcUbi16 | 31.07 | 29.70 | 1.37 |
| D35S16 | 32.09 | 27.85 | 4.25 | PcUbi17 | 31.85 | 29.77 | 2.08 |
| D35S17 | 30.03 | 27.88 | 2.16 | PcUbi18 | 32.01 | 29.66 | 2.36 |
| D35S18 | 31.44 | 28.35 | 3.09 | PcUbi19 | 32.37 | 29.43 | 2.94 |
| D35S19 | 31.57 | 28.17 | 3.41 | PcUbi20 | 35.12 | 30.09 | 5.03 |
| D35S20 | 30.28 | 28.20 | 2.08 | PcUbi21 | 31.30 | 29.59 | 1.71 |
| D35S21 | 32.32 | 29.08 | 3.24 | PcUbi22 | 30.16 | 29.18 | 0.98 |
| D35S22 | 29.44 | 28.12 | 1.32 | PcUbi23 | 33.66 | 29.24 | 4.42 |
| D35S23 | 27.00 | 28.06 | −1.06 | PcUbi24 | 29.88 | 27.85 | 2.03 |
| D35S24 | 28.39 | 27.24 | 1.15 | PcUbi25 | 37.94 | 29.16 | 8.78 |
| D35S25 | 29.66 | 27.01 | 2.65 | PcUbi26 | 29.94 | 29.43 | 0.51 |
| D35S26 | 30.40 | 27.56 | 2.84 | PcUbi27 | 32.27 | 29.03 | 3.24 |
| D35S27 | 29.16 | 26.98 | 2.18 | PcUbi28 | 30.99 | 29.17 | 1.82 |
| D35S28 | 27.22 | 28.27 | −1.05 | PcUbi29 | 31.14 | 29.05 | 2.09 |
| D35S29 | 26.32 | 27.30 | −0.98 | PcUbi30 | 29.97 | 29.34 | 0.63 |
| D35S30 | 28.77 | 27.54 | 1.23 | PcUbi31 | 33.97 | 29.69 | 4.29 |
| D35S31 | 29.77 | 27.23 | 2.54 | PcUbi32 | 27.26 | 27.09 | 0.18 |
| D35S32 | 28.35 | 27.60 | 0.75 | PcUbi33 | 29.41 | 28.81 | 0.60 |
| D35S33 | 31.34 | 27.41 | 3.93 | PcUbi34 | 32.83 | 29.09 | 3.74 |
| D35S34 | 39.05 | 28.03 | 11.02 | PcUbi35 | 28.96 | 28.62 | 0.35 |
| D35S35 | 27.61 | 27.75 | −0.14 | PcUbi36 | 33.75 | 29.03 | 4.72 |
| D35S36 | 40.00 | 27.62 | 12.38 | PcUbi37 | 30.65 | 28.22 | 2.43 |
| D35S37 | 29.74 | 28.15 | 1.59 | PcUbi38 | 31.25 | 30.22 | 1.04 |
| D35S38 | 29.12 | 27.42 | 1.70 | PcUbi39 | 29.11 | 28.93 | 0.18 |
| D35S39 | 27.25 | 27.60 | −0.34 | PcUbi40 | 27.02 | 26.99 | 0.04 |
| D35S40 | 29.83 | 27.72 | 2.11 | PcUbi41 | 30.82 | 29.69 | 1.13 |
| D35S41 | 34.31 | 28.21 | 6.10 | PcUbi42 | 33.73 | 34.80 | −1.07 |
| D35S42 | 33.09 | 28.32 | 4.77 | PcUbi43 | 30.90 | 30.41 | 0.49 |
| D35S43 | 29.91 | 28.36 | 1.55 | PcUbi44 | 32.39 | 30.15 | 2.25 |
| D35S44 | 32.17 | 28.07 | 4.10 | PcUbi45 | 28.45 | 30.14 | −1.69 |
| D35S45 | 30.74 | 28.31 | 2.43 | PcUbi46 | 29.88 | 30.07 | −0.19 |
| D35S46 | 40.00 | 28.41 | 11.59 | PcUbi47 | 34.13 | 32.72 | 1.41 |
| D35S47 | 32.05 | 28.03 | 4.02 | PcUbi48 | 29.65 | 28.31 | 1.34 |
| D35S48 | 30.98 | 28.02 | 2.96 | | | | |

Example 10

Investigation of the Stability of the Level of GUS Expression in Leaves of Transgenic T2 *Arabidopsis* Plants 12 T1 lines were selected from each construct, in order to determine expression of GUS in the progeny. For this purpose, 10 offsprings of each line were cultivated and leaves were harvested 3 weeks after seeding, and the amount of GUS transcript was determined by means of qPCR as described.

The range of variation within the T2 of a line is smaller in the progeny of the 1bxPcUbiGUS plants (table 4).

TABLE 4

Determination of GUS expression in progeny of transgenic *Arabidopsis* plants. The median of delta Ct values from the measurement of in each case 10 T2 plants of each line and the range of measured data are indicated.

| Median d35S | Range d35S | Median PcUbi | Range PcUbi |
|---|---|---|---|
| 0.92 | 1.09 | 3.81 | 1.28 |
| 0.46 | 1.18 | 1.47 | 1.42 |
| 3.00 | 1.51 | −0.56 | 1.47 |
| 1.00 | 2.13 | 1.79 | 1.58 |
| 1.28 | 2.16 | 1.26 | 1.68 |
| −0.77 | 2.55 | 1.28 | 1.97 |
| 0.11 | 2.80 | 0.22 | 2.05 |
| 2.12 | 2.84 | −0.13 | 2.24 |
| 5.18 | 4.16 | 1.39 | 2.33 |
| 2.50 | 4.94 | 0.10 | 2.65 |
| 2.65 | 5.92 | 1.38 | 2.97 |
| 6.27 | 7.91 | 6.69 | 4.15 |

Equivalents

The skilled worker knows, or can identify, by using merely routine experiments, a large number of equivalents of the specific embodiments, described herein, of the invention. These equivalents are intended to be included in the patent claims.

DESCRIPTION OF THE INVENTION

Other embodiments and advantages of the invention are set forth in part in the description, which follows, and in part, may be obvious from this description, or may be learned from the practice of the invention. All references cited herein, including all U.S. and foreign patents and patent applications, and all publications or other documentary materials, are specifically and entirely hereby incorporated herein by reference. It is intended that the specification and examples be considered exemplary only.

We claim:

1. A process for constitutive expression of a nucleic acid in a transgenic dicotyledonous plant under the control of a parsley ubiquitin promoter, wherein the process comprises:
   a) linking the nucleic acid to a promoter to form a construct, wherein the promoter comprises
      i) the sequence as set forth in SEQ ID NO: 1 or a functional fragment thereof which has the same promoter activity as the sequence of SEQ ID NO: 1, or
      ii) a sequence having 90% or more sequence identity to the sequence of SEQ ID NO: 1 and having the same expression activity as the full-length sequence of SEQ ID NO: 1; and
   b) introducing into a plant the construct under conditions which enable the nucleic acid to be stably integrated into the genome of the plant;
   wherein the promoter is heterologous to the nucleic acid sequence; and
   wherein the nucleic acid is constitutively expressed in the plant.

2. The process of claim 1, wherein the nucleic acid is functionally linked to one or more further regulatory sequences.

3. The process of claim 1, wherein the nucleic acid functions as a selection marker, a reporter gene, or encodes a protein selected from the group consisting of an enzyme, a protein which mediates resistance to insects, a protein which mediates resistance to viruses, a protein which mediates resistance to bacteria, a protein which mediates resistance to fungi, a protein which mediates resistance to nematodes, a protein which mediates in plants resistance to drought, a protein which mediates in plants resistance to cold, a protein which mediates in plants resistance to heat, a protein which mediates in plants resistance to salt, an inhibitor, a lectin, an RNAase, a ribozyme, an antibody, a vaccine, a pharmaceutical, an anti-freezing protein, a cytochrome P-450 protein, a transcription activator, a transcription repressor, and a protein involved in the biosynthesis of fine chemicals.

4. The process of claim 3, wherein the protein involved in the biosynthesis of fine chemicals is a protein involved in fatty acid metabolism, amino acid metabolism, vitamin metabolism, carotenoid metabolism, or carbohydrate metabolism.

5. The process of claim 1, wherein the construct contains one or more further genes under the control of the parsley ubiquitin promoter or of another promoter.

6. The process of claim 1, wherein the nucleic acid is expressed in the sense or antisense direction or in the sense and antisense directions.

7. The process of claim 1, wherein the construct is inserted between two T-DNA sections.

8. The process of claim 1, wherein the dicotyledonous plant is selected from the group consisting of oilseed rape, evening primrose, canola, peanut, verbascum, thistle, hazelnut, almond, macadamia, avocado, bay, wild roses, pumpkin, pistachios, sesame, linseed, sunflower, safflower, soybean, borage, poppy, mustard, hemp, castor-oil plant, olive, calendula, punica, sugar beet, tomato, potato, tobacco, carrot, poplar, cotton, manioc, pepper, *tagetes,* eggplant, pea, alfalfa, coffee, cocoa, tea, walnut, and *Arabidopsis.*

9. The process of claim 1, wherein the process further comprises culturing the transgenic plant, and isolating a product produced in the transgenic plant due to expression of the nucleic acid.

10. A nucleic acid construct for stably expressing a nucleic acid in a transgenic plant comprising:
    a) a promoter comprising:
       i) the sequence of SEQ ID NO: 1 or a functional fragment thereof which has the same promoter activity as the sequence of SEQ ID NO: 1, or
       ii) a sequence having 90% or more sequence identity to the sequence of SEQ ID NO: 1 and having the same expression activity as the full-length sequence of SEQ ID NO: 1; and
    b) a nucleic acid to be expressed transgenically;
    wherein the promoter is operably linked and heterologous to the nucleic acid to be expressed transgenically.

11. The nucleic acid construct of claim 10, which comprises at least one further element selected from the group consisting of:
    a) one or more further genetic control sequences functionally linked to the nucleic acid to be expressed,
    b) one or more additional functional elements,
    c) a polylinker located between the promoter and the nucleic acid to be expressed, and
    d) at least one further nucleic acid under control of a promoter having the sequence of SEQ ID NO: 1 or a functional fragment thereof having the same promoter activity, or of a promoter having a sequence having 90% or more sequence identity to the sequence of SEQ ID NO: 1 and having the same expression activity as the full-length sequence of SEQ ID NO: 1, or of another promoter.

12. The nucleic acid construct of claim 10, which is inserted between two T-DNA sections.

13. The nucleic acid construct of claim 10, wherein the nucleic acid to be expressed transgenically is selected from the group consisting of a selection marker, a reporter gene, an RNAi construct, an enzyme, a protein which mediates resistance to insects, viruses, bacteria, fungi or nematodes, a nucleic acid sequence or a protein which mediates in plants resistance to drought, cold, heat or salt, an inhibitor, a lectin, an RNAase, a ribozyme, an antibody, a vaccine, a pharmaceutical, an anti-freezing protein, a cytochrome P-450 protein, a transcription activator or repressor, and a protein involved in the biosynthesis of fine chemicals.

14. A vector, comprising the nucleic acid construct of claim 10.

15. A dicotyledonous transgenic plant cell, plant or part thereof, comprising the nucleic acid construct of claim 10.

16. The dicotyledonous transgenic plant of claim 15, wherein the plant is selected from the group consisting of oilseed rape, evening primrose, canola, peanut, verbascum, thistle, hazelnut, almond, macadamia, avocado, bay, wild roses, pumpkin, pistachios, sesame, linseed, sunflower, safflower, soybean, borage, poppy, mustard, hemp, castor-oil plant, olive, calendula, punica, sugar beet, tomato, potato, tobacco, carrot, poplar, cotton, manioc, pepper, *tagetes,* eggplant, pea, alfalfa, coffee, cocoa, tea, walnut, and *Arabidopsis.*

17. A method for preparing foodstuffs, feedstuffs, seeds, cosmetics, pharmaceuticals or fine chemicals comprising utilizing the transgenic plant of claim 15, or products obtained from said plant wherein said products comprise said nucleic acid construct, in the production of feedstuffs, foodstuffs, seeds, fine chemicals, cosmetics or pharmaceuticals.

18. The process of claim 1, wherein the promoter comprises the sequence as set forth in SEQ ID NO: 1 or a functional fragment thereof which has the same promoter activity as the sequence of SEQ ID NO: 1.

19. The process of claim 1, wherein the promoter comprises a sequence having 90% or more sequence identity to the sequence of SEQ ID NO: 1 and having the same expression activity as the full-length sequence of SEQ ID NO: 1.

20. The process of claim 1, wherein the promoter comprises a sequence having 95% or more sequence identity to the sequence of SEQ ID NO: 1 and having the same expression activity as the full-length sequence of SEQ ID NO: 1.

21. The nucleic acid construct of claim 10, wherein the promoter comprises the sequence of SEQ ID NO: 1.

22. The nucleic acid construct of claim 10, wherein the promoter comprises a functional fragment of the sequence of SEQ ID NO: 1 which has the same promoter activity as the sequence of SEQ ID NO: 1.

23. The nucleic acid construct of claim 10, wherein the promoter comprises a sequence having 90% or more sequence identity to the sequence of SEQ ID NO: 1 and having the same expression activity as the full-length sequence of SEQ ID NO: 1.

24. The nucleic acid construct of claim 10, wherein the promoter comprises a sequence having 95% or more sequence identity to the sequence of SEQ ID NO: 1 and having the same expression activity as the full-length sequence of SEQ ID NO: 1.

* * * * *